(12) United States Patent
Bossenmaier et al.

(10) Patent No.: US 7,259,262 B2
(45) Date of Patent: Aug. 21, 2007

(54) ARYLAZOLE DERIVATIVES, THEIR MANUFACTURE AND USE AS PHARMACEUTICAL AGENTS

(75) Inventors: Birgit Bossenmaier, Seefeld (DE); Walter-Gunar Friebe, Mannheim (DE); Ulrike Reiff, Penzberg (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 389 days.

(21) Appl. No.: 10/965,996

(22) Filed: Oct. 15, 2004

(65) Prior Publication Data

US 2005/0124670 A1    Jun. 9, 2005

(30) Foreign Application Priority Data

Oct. 24, 2003  (EP) .................................. 03024399
Oct. 28, 2003  (EP) .................................. 03024694
Nov. 13, 2003  (EP) .................................. 03025948

(51) Int. Cl.
  C07D 263/32  (2006.01)
  C07D 277/22  (2006.01)
  A01N 43/76   (2006.01)
  A01N 43/78   (2006.01)
(52) U.S. Cl. ...................... 548/235; 548/235; 548/202; 514/365; 514/374
(58) Field of Classification Search ..................... None
See application file for complete search history.

(56) References Cited

U.S. PATENT DOCUMENTS

2005/0203064 A1* 9/2005 Bossenmaier et al. ........ 514/79

FOREIGN PATENT DOCUMENTS

EP    1 350 793      10/2003
WO    WO98/03505    1/1998
WO    WO 01/077107  10/2001
WO    WO 03/031442 A  4/2003
WO    WO 03/059907   7/2003

OTHER PUBLICATIONS http://www.forbes.com/2004/04/26/042automarketscan03_print.html, p. 1 of 3.*
http://www.gene.com/gene/products/information/oncology/tarceva/index.jsp, pp. 1-3 of 4.*
Baselga, J. et al, Oncology 63 (Suppl. 1) (2002) 6-16.
Chan, A.C. et al, Curr. Opin. Immunol. 8 (196) 394-401.
Larsen et al, Ann. Reports in Med. Chem. (1989) Chpt. 13.
Ranson, M. et al, Oncology 63 (Suppl. 1) (2002) 17-24.
Wilks et al, Prog. Growth Factor Res. 2 (1990) 97-111.
Wright, C., et al, Br. J. Cancer 65 (1992) 118-121.
Yarden, Y. et al, Annu. Rev. Biochem. 57 (1988) 443-478.

* cited by examiner

Primary Examiner—Cecilia J. Tsang
Assistant Examiner—Sun Jae Y Loewe
(74) Attorney, Agent, or Firm—George W. Johnston; Patricia S. Rocha-Tramaloni; Gene J. Yao

(57) ABSTRACT

There are presented compounds of formula (I)

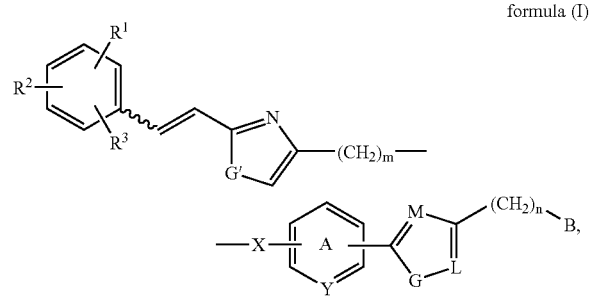

formula (I)

their pharmaceutically acceptable salts, enantiomeric forms thereof, diastereoisomers and racemates, the preparation of the above-mentioned compounds, medicaments containing them and their manufacture, as well as the use of the above-mentioned compounds in the control or prevention of illnesses such as cancer.

18 Claims, No Drawings

ARYLAZOLE DERIVATIVES, THEIR MANUFACTURE AND USE AS PHARMACEUTICAL AGENTS

The present invention relates to novel arylazole derivatives, to a process for their manufacture, medicaments containing them and their manufacture as well as the use of these compounds as pharmaceutically active agents.

BACKGROUND OF THE INVENTION

Protein tyrosine kinases (PTKs) catalyse the phosphorylation of tyrosyl residues in various proteins involved in the regulation of cell growth and differentiation (Wilks et al., Prog. Growth Factor Res. 2 (1990) 97-111; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukaemia and ovarian, bronchial and pancreatic cancer. High levels of these receptors correlate with poor prognosis and response to treatment (Wright, C., et al., Br. J. Cancer 65 (1992) 118-121). Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (Suppl. 1) (2002) 17-24). However there remains a need for new compounds with improved therapeutic properties, such as improved activity, solubility, tolerability, selectivity or stability to name only a few.

SUMMARY OF THE INVENTION

The present invention relates to compounds of the formula

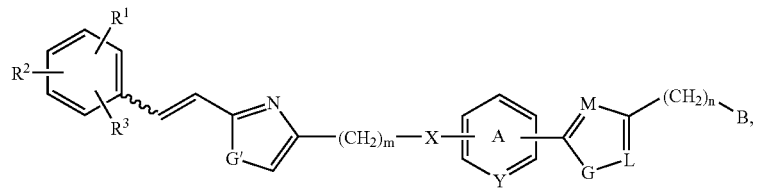

and the pharmaceutically acceptable salts thereof, wherein $R^1$, $R^2$, $R^3$, G', G, L, M, A, B, X and n are as described in this application. These compounds are believed to show activity as inhibitors of the HER-signalling pathway and, as such, have antiproliferative activity.

DETAILED DESCRIPTION OF THE INVENTION

The present invention relates to new compounds of the general formula (I),

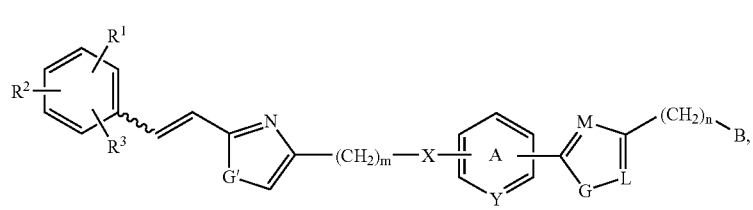

formula (I)

wherein $R^1$, $R^2$ and $R^3$ are each independently hydrogen, halogen, nitro, cyano, —$SF_5$, —$NR^5R^{5'}$, $R^6C(O)$—, $R^7O$—, $R^7S(O)_x$—, $R^7OC(O)$—, $R^6C(O)O$—, $R^6C(O)NR^5$—, and $R^5R^{5'}NC(O)$—; or a group chosen from aliphatic hydrocarbon, alicyclic hydrocarbon, aromatic hydrocarbon, non-aromatic heterocyclic groups, aromatic heterocyclic groups, which groups are unsubstituted or substituted by aliphatic hydrocarbon groups, alicyclic hydrocarbon groups, aromatic hydrocarbon groups, non-aromatic heterocyclic groups, halogen, nitro, cyano, azido, —$NR^5R^{5'}$, $R^6CO$—, $R^7O$—, $R^7S(O)_x$—, $R^7OC(O)$—, $R^6C(O)O$—, $R^6C(O)NR^5$— and $R^5R^{5'}NC(O)$— group; or $R^1$ and $R^2$ together with the carbon atoms to which they are attached form a 5 or 6 membered heterocyclic ring; and $R^3$ is hydrogen or halogen;

X is —O—, —$S(O)_x$—, or —$NR^4$—;

x is 0, 1 or 2;

$R^4$ is hydrogen or $C_1$-$C_6$ alkyl;

$R^5$ and $R^{5'}$ are independently of each other hydrogen or a group chosen from aliphatic hydrocarbon, alicyclic hydrocarbon, aromatic hydrocarbon, non-aromatic heterocyclic, or $R^6C(O)$—;

$R^6$ is hydrogen or a group chosen from aliphatic hydrocarbon, alicyclic hydrocarbon, aromatic hydrocarbon, non-aromatic heterocyclic or $R^7S$—;

R⁷ is hydrogen or a group chosen from aliphatic hydrocarbon, alicyclic hydrocarbon, aromatic hydrocarbon, non-aromatic heterocyclic, halogen, or R⁶C(O)—;

R⁵, R⁵', R⁶, R⁷ are optionally further substituted;

Y is for =CH— or =N—;

L and M are independently =CH—, or =N—,

G and G' are —CH₂—, —NH—, —S— or —O—, with the proviso that at least one of G, L or M contains or represents nitrogen;

m is an integer of 1 to 5;

n is an integer of 0 to 10;

B is an optionally substituted aromatic azole ring; and ring A may optionally further be substituted;

the symbol means either (E)- or (Z)-configuration of the arylvinyl group wherein it is used; and their pharmaceutically acceptable salts.

The compounds of the present invention show activity as inhibitors of the HER-signalling pathway and therefore possess anti-proliferative activity. Objects of the present invention are the compounds of formula (I) and their pharmaceutically acceptable salts, enantiomeric forms, diastereoisomers and racemates, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

More specifically, the present invention is to provide (1) the heterocyclic compound (I) or a salt thereof;

(2) a pharmaceutical composition, containing one or more compounds of formula (I) together with pharmaceutically acceptable excipients;

(3) a pharmaceutical composition as defined above for the inhibition of tumor growth;

(4) the use of a compound of formula (I) for the treatment of cancer;

(5) the use of a compound of formula (I) for the manufacture of medicaments for the inhibition of tumor growth;

(6) a method of producing the compounds of formula (I) or a salt thereof.

The term "aliphatic hydrocarbon group" denotes a straight-chain or branched alkyl group having 1 to 15 carbon atoms, or an unsaturated straight-chain or branched aliphatic hydrocarbon group having 2 to 15 carbon atoms such as alkenyl group or alkynyl group. Examples of the "alkyl groups" include $C_{1-15}$ alkyl groups, more preferably $C_{1-6}$ alkyl groups such as methyl, ethyl, propyl, isopropyl, butyl, isobutyl, sec.-butyl, tert.-butyl, pentyl, isopentyl, neopentyl, tert.-pentyl, hexyl, isohexyl, heptyl, octyl, nonyl, decyl, 1,1-dimethylbutyl, 2,2-dimethylbutyl, 3,3-dimethylbutyl and 2-ethylbutyl.

Examples of the "alkenyl group" include $C_{2-15}$ alkenyl groups, more preferably $C_{2-6}$ alkenyl groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenul, and 5-hexenyl.

Examples of the "alkynyl group" include $C_{2-15}$ alkynyl groups, more preferably $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "alicyclic hydrocarbon group" denotes a saturated or unsaturated cycloalkyl group, cycloalkenyl group, cycloalkadienyl group or partially unsaturated condensed bicyclic hydrocarbon group having 3 to 12 carbon atoms.

Examples of the "cycloalkyl group" include $C_{3-12}$ cycloalkyl groups such as cyclopropyl, cyclobutyl, cyclopentyl, cyclohexyl, cycloheptyl and cyclooctyl; and $C_{6-10}$ bicycloalkyl groups such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Examples of the "cycloalkenyl group" include $C_{5-10}$ cycloalkenyl groups such as 2-cyclopenten-1-yl, 3-cyclopenten-1-yl, 2-cyclohexen-1-yl and 3-cyclohexen-1-yl.

Examples of the "cycloalkadienyl group" include $C_{5-12}$ cycloalkadienyl groups such as 2,4-cyclopentadien-1-yl, 2,4-cyclohexadien-1-yl and 2,5-cyclohexadien-1-yl.

Examples of the "partially unsaturated condensed bicyclic hydrocarbon group" include groups having 9 to 12 carbon atoms. Examples of such groups are dihydronaphthyl groups such as 3,4-dihydro-2-naphthyl; and tetrahydronaphthyl such as 1,2,3,4-tetrahydronaphthyl.

The term "aromatic hydrocarbon group" denotes a monocyclic or a condensed polycyclic aromatic hydrocarbon group, preferably exemplified by $C_{6-14}$ aryl groups such as phenyl, naphthyl, anthryl, phenanthryl, acenaphthylenyl and 9-fluorenone-2-yl, especially monocyclic or condensed bicyclic aromatic hydrocarbon groups such as phenyl, 1-naphthyl and 2-naphthyl.

The term "non-aromatic heterocyclic groups" includes 3- to 7-membered non-aromatic heterocyclic groups containing 1 or 2 hetero atoms selected from nitrogen, oxygen and sulfur, examples of such groups are oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

The term "aromatic heterocyclic groups" denotes 5- or 6-membered aromatic monocyclic heterocyclic groups having 1 to 4 heteroatoms chosen from nitrogen atom, oxygen atom or sulfur atom. Examples of such aromatic heterocyclic groups include pyridyl (e.g. 2-pyridyl, 3-pyridyl, 4-pyridyl), pyrimidinyl (2-pyrimidinyl, 5-pyrimidinyl, 6-pyrimidinyl), 6-pyridazinyl (e.g. 3-pyridazinyl, 4-pyridazinyl), pyrazinyl (e.g. 2-pyrazinyl), pyrrolyl (e.g. 1-pyrrolyl, 2-pyrrolyl), imidazolyl (e.g. 1-imidazolyl, 2-imidazolyl, 4-imidazolyl, 5-imidazolyl), pyrazolyl (e.g. 1-pyrazolyl, 3-pyrazolyl, 4-pyrazolyl), isoxazolyl, isothiazolyl, thiazolyl (e.g. 2-thiazolyl, 4-thiazolyl, 5-thiazolyl), oxazolyl (e.g. 2-oxazolyl, 4-oxazolyl, 5-oxazolyl), oxadiazolyl (e.g. 1,2,4-oxadiazolyl such as 1,2,4-oxadiazol-5-yl, 1,2,3-oxadiazolyl, 1,3,4-oxadiazolyl), thiadiazolyl (e.g. 1,2,3-thiadiazolyl, 1,2,4-thiadiazolyl, 1,3,4-thiadiazolyl), triazolyl (e.g. 1,2,4-triazolyl such as 1,2,4-triazol-1-yl, 1,2,4-triazol-5-yl, 1,2,3-triazolyl such as 1,2,3-triazol-1-yl, 1,2,3-triazol-2-yl, 1,2,3-triazol-4-yl), tetrazolyl (e.g. tetrazol-1-yl, tetrazol-5-yl), benzimidazolyl (e.g. benzimidazol-1-yl, benzimidazol-2-yl), indolyl (e.g. indol-1-yl, indol-3-yl), indazolyl (e.g. 1H-indazol-1-yl, 1H-indazol-3-yl), pyrrolopyrazinyl (e.g. 1H-pyrrolo[2,3-b]pyrazinyl), pyrrolopyridyl (e.g. 1H-pyrrolo[2,3-b]pyridyl), imidazopyridyl (e.g. 1H-imidazo[4,5-b]pyridyl, 1H-imidazo[4,5-c]pyridyl, imidazopyrazinyl (e.g. 1H-imidazo[4,5-b]pyrazinyl), pyrrolopyridazinyl (e.g. pyrrolo[1,2-b]pyridazinyl), pyrazolopyridyl (e.g. pyrazolo[1,5-a]pyridyl), imidazopyridyl (e.g. imidazo[1,2-a]pyridyl, imidazo[1,5-a]pyridyl), imidazopyridazinyl (e.g. imidazo[1,2-b]pyridazinyl), imidazopyrimidinyl (e.g. imidazo[1,2-a]pyrimidinyl), furyl, thienyl, benzofuranyl, benzothienyl (e.g. benzo[b]thienyl), benzoxazolyl, benzthiazolyl, quinolyl, isoquinolyl or quinazolinyl. Preferable examples include 5-membered cyclic aromatic azole groups such as oxazolyl, thiazolyl, isoxazolyl, isothiazolyl, imidazolyl, triazolyl, oxadiazolyl and thiadiazolyl.

The term "aromatic heterocyclic groups" further denotes aromatic condensed heterocyclic group formed by condensation of a 5- or 6-membered aromatic heterocyclic group containing, 1 to 4 hetero atoms selected from nitrogen, oxygen and sulfur with (i) a 5- or 6-membered aromatic or a non-aromatic heterocyclic group containing 1 or 2 nitrogen atoms, or with (ii) a benzene ring or with (iii) a 5-membered aromatic or non-aromatic heterocyclic group containing one sulfur. Examples of such condensed rings are benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1,3-benzodioxolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[of 1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

The term "optionally substituted aromatic azole ring" represents (1) a 5-membered aromatic monocyclic heterocyclic group containing 1 to 4 nitrogen atoms and optionally one oxygen atom or one sulfur atom, or (2) an aromatic condensed heterocyclic group formed by condensation of a 5-membered aromatic heterocyclic ring containing 1 to 4 nitrogen atoms and optionally containing one oxygen atom or one sulfur atom with (i) a 5- or 6-membered aromatic or non-aromatic heterocyclic group containing one or two nitrogen atoms, or with (ii) a benzene ring or with (iii) a 5-membered aromatic or non-aromatic heterocyclic group containing one sulfur atom.

Examples of such "aromatic azole rings" are pyrrolyl (e.g. 1-pyrrolyl), imidazolyl (e.g. 1-imidazolyl, 2-imidazolyl), pyrazolyl (e.g. 1-pyrazolyl), triazolyl (e.g. 1,2,4-triazol-1-yl, 1,2,3-triazol-1-yl, 1,2,3-triazol-4-yl), tetrazolyl (e.g. tetrazol-1-yl, tetrazol-5-yl), benzimidazolyl (e.g. benzimidazol-1-yl), indolyl (e.g. indol-1-yl), indazolyl (e.g. 1H-indazol-1-yl), pyrrolopyrazinyl (e.g. 1H-pyrrolo[2,3-b]pyrazin-1-yl), pyrrolopyridyl (e.g. 1H-pyrrolo [2,3-b]pyridin-1-yl), imidazopyridyl (e.g. 1H-imidazo[4,5-b]pyridin-1-yl), and imidazopyrazinyl (e.g. 1H-imidazo[4,5-b]pyrazin-1-yl), especially imidazolyl and triazolyl group.

The "aromatic azole ring" may be optionally substituted by 1 to 3 (preferably one or two) substituents at any substitutable position. Examples of the substituents include aliphatic hydrocarbon groups, alicyclic hydrocarbon groups, aromatic hydrocarbon groups, non-aromatic heterocyclic groups, aromatic heterocyclic groups, halogen atom, nitro group, cyano group, a $NR^5R^{5'}$ group, a $R^6CO$ group, a $R^7O$— group, a $R^7S(O)_x$— group (wherein x has the meaning given above), a $R^7OC(O)$— group, a $R^6C(O)O$— group, a $R^6C(O)NR^5$— group or a $R^5R^{5'}NC(O)$— group.

Preferred aromatic azole rings include the pyrrolyl group, imidazolyl group, pyrazolyl group, triazolyl group, tetrazolyl group or benzimidazolyl group respectively substituted with 1 or 2 substituents selected from (i) alkyl groups (e.g. $C_{1-15}$ alkyl group), (ii) aryl groups (e.g. phenyl group), (iii) hydroxyalkyl groups (e.g. hydroxy-$C_{1-5}$ alkyl group), (iv) carboxyl groups, (v) alkoxycarbonyl groups (e.g. $C_{2-7}$ alkoxycarbonyl group) and (vi) carbamoyl groups, and the imidazolyl group and triazolyl group are more preferable.

"Halogen" denotes fluorine, chlorine, bromine and iodine, especially fluorine and chlorine. Examples of the "$NR^5R^{5'}$ group" are amino, N-mono($C_{1-6}$)alkylamino groups, N,N-di($C_{1-6}$)alkylamino groups such as methylamino, dimethylamino, ethylamino, diethylamino, butylamino, dibutylamino, diallylamino, cyclohexylamino, acetylamino, propionylamino, benzoylamino, phenylamino, and N-methyl-N-phenylamino.

Examples of the "$R^6C(O)$— group" are HCO, a $C_{1-6}$-alkyl-CO group such as acetyl, propionyl, butyryl, isobutyryl, valeryl, isovaleryl, pivaloyl, hexanoyl, heptanoyl and octanoyl, a $C_{3-12}$-cycloalkyl-CO— group such as cyclobutanecarbonyl, cyclopentanecarbonyl, cyclohexanecarbonyl and cycloheptanecarbonyl, a $C_{2-6}$-alkenyl-CO group such as crotonoyl, a $C_{5-10}$ cycloalkenyl-CO— group such as 2-cyclohexenecarbonyl, a $C_{6-14}$ aromatic hydrocarbon-CO— group such as phenyl-CO and naphthyl-CO and an aromatic heterocyclic-CO— such as pyridyl-CO.

Examples of "$R^7O$— groups" are the hydroxyl group or a $C_1$-$C_{15}$-alkoxy group wherein the "alkyl" part is as defined above. Such groups are for example as methoxy, ethoxy, propoxy, isopropoxy, butoxy, isobutoxy, sec.-butoxy, tert.-butoxy, pentyloxy, isopentyloxy, neopentyloxy, hexyloxy, heptyloxy and nonyloxy; $C_3$-$C_{12}$-cycloalkyloxy group such as cyclobutoxy, cyclopentyloxy and cyclohexyloxy; $C_2$-$C_{15}$-alkenyloxy group such as allyloxy, crotyloxy, 2-pentenyloxy and 3-hexenyloxy, $C_5$-$C_{10}$-cycloalkenyloxy group such as 2-cyclopentenyloxy and 2-cyclohexenyloxy; $C_{6-14}$-aryloxy group or a aralkyloxy group such as phenyl-$C_{1-6}$-alkoxy group (e.g. benzyloxy and phenethyloxy) and naphthyl-$C_{1-6}$ alkoxy group.

Examples of the "$R^7S(O)_x$— group" include the mercapto group or $C_{1-15}$ alkylthio group, $C_{3-12}$ cycloalkylthio group, $C_{2-15}$ alkenylthio group, $C_{7-12}$-aralkylthio group, $C_{6-14}$-arylthio group, heteroarylthio group, heteroarylalkylthio group and acylthio group, all of which may optionally be oxidized to sulfinyl or sulfonyl.

Examples of the $C_{1-15}$ alkylthio groups are methylthio, ethylthio, propylthio, isopropylthio, butylthio, isobutylthio, sec.-butylthio, tert.-butylthio, pentylthio, isopentylthio, neopentylthio, hexylthio, heptylthio and nonylthio.

Examples of the $C_{3-12}$ cycloalkylthio groups are cyclobutylthio, cyclopentylthio and cyclohexylthio.

Examples of the $C_{2-15}$ alkenylthio groups are allylthio, crotylthio, 2-pentenylthio and 3-hexenylthio.

Examples of the $C_{7-20}$ aralkylthio groups are phenyl-$C_{1-6}$ alkylthio (e.g. benzylthio and phenethylthio), and naphthyl-$C_{1-6}$ alkylthio.

Examples of the acylthio group include $C_{2-15}$ acylthio groups such as $C_{2-7}$ alkanoylthio groups (e.g. acetylthio, propionylthio, butyrylthio and isobutyrlthio) or $C_{6-14}$ arylcarbonylthio (e.g. benzoylthio and naphthoylthio).

Examples of the "$R^7OC(O)$— group" are alkoxy carbonyl groups wherein the alkyl part is as defined above, or aryloxycarbonyl groups.

Preferable examples of the alkoxycarbonyl groups include $C_{2-7}$ alkoxycarbonyl groups such as methoxycarbonyl, ethoxycarbonyl, propoxycarbonyl and butoxycarbonyl.

Preferable examples of the aryloxycarbonyl group include $C_{7-15}$ aryloxycarbonyl groups optionally substituted with $C_{1-3}$ alkyl groups, or $C_{1-3}$ alkoxy groups, halogen, nitro group, hydroxyl group or amino group, such as phenoxycarbonyl and p-tolyloxycarbonyl.

Examples of $R^6C(O)O$ are the formyl group or $C_{2-7}$ alkylcarboxyl groups such as acetyloxy, propionyloxy, butanoyloxy and pentanoyloxy.

Examples of $R^6C(O)NR^5$ are $C_{2-8}$ alkanoylamino groups such as acetylamino and propionylamino or $C_{7-15}$ arylcarbonylamino groups such as benzoylamino and naphthoylamino.

Examples of the "$R^5R^{5'}NC(O)$— group" wherein $R^5$ and $R^{5'}$ independently stand for H and optionally substituted hydrocarbon groups or optionally substituted heterocyclic groups, are the carbamoyl group, N-mono($C_{1-6}$)alkylcarbamoyl groups, N,N-di($C_{1-6}$)alkylcarbamoyl groups such as N-methylcarbamoyl, N-ethylcarbamoyl, N,N-dimethylcarbamoyl and N,N-diethylcarbamoyl.

A "5 or 6 membered heterocyclic ring" as used herein denotes a non-aromatic, monocyclic ring consisting of 5 or 6 ring atoms of which one or two may independently be selected from S, N or O and the remaining atoms being carbon atoms. Said "5 or 6 membered heterocyclic ring" may be fused to another aromatic or non-aromatic hetero- or carbocyclic, 6-membered ring. Examples for such 5 or 6 membered heterocyclic rings are pyrrolidine, imidazolidine, thiazolidine, oxazolidine, tetrahydro-furan, [1,3]dioxolane, [1,3]oxathiolane, tetrahydro-thiophene, pyrazolidine, tetrahydro-pyran, piperidine, piperazine, morpholine and thiomorpholine.

Said 5 or 6 membered heterocyclic ring is preferably fused to phenyl. Examples for such fused ring systems are indoline; isoindoline; 2,3-dihydro-benzo[b]thiophene; 2,3-dihydro-benzofuran; benzo [1,3]dioxole; benzo [1,3]oxathiole; 2,3-dihydro-benzoxazole; 2,3-dihydro-benzothiazole; 2,3-dihydro-1H-benzimidazole; 2,3-dihydro-1H-indazole; 3,4-dihydro-2H-benzo[1,4]thiazine; 3,4-dihydro-2H-benz[1,4]oxazine or 1,2,3,4-tetrahydro-quinoxaline.

The aliphatic hydrocarbon groups, alicyclic hydrocarbon groups, aromatic hydrocarbon groups, non-aromatic heterocyclic groups and aromatic heterocyclic groups of residues $R^1$, $R^2$, $R^3$, as well as $R^5$, $R^{5'}$, $R^6$, and $R^7$ may be further substituted by one or several groups chosen from aliphatic hydrocarbon groups, alicyclic hydrocarbon groups, aromatic hydrocarbon groups, non-aromatic heterocyclic groups, halogen, nitro, cyano, azido, —$NR^5R^{5'}$, $R^6CO$—, $R^7O$—, $R^7S(O)_x$— wherein x is 0, 1 or 2, $R^7OC(O)$, $R^6C(O)O$, $R^6C(O)NR^5$— and $R^5R^{5'}NC(O)$ group.

Examples of such substituted groups are, but not limited to, a) substituted $C_{1-6}$ alkyl groups such as for example, trifluoromethyl, difluoromethyl, 2,2,2-trifluoroethyl, trichloromethyl, hydroxymethyl, methoxymethyl, 2-methoxyethyl and 2,2-dimethoxyethyl;

b) $C_{1-6}$ alkyl group substituted with 1 to 3 $C_{6-14}$ aryl groups (e.g. $C_{1-6}$ alkyl group substituted with 1 to 3 phenyl groups such as benzyl, 2-phenylethyl, 1,2-diphenylethyl and 2,2-diphenylethyl);

c) $C_{2-6}$ alkenyl groups substituted with 1 to 3 $C_{6-14}$ aryl groups (e.g. $C_{2-6}$ alkenyl groups substituted 1 to 3 phenyl groups, such as (E)-2-phenylethenyl, (Z)-2-phenylethenyl, 2,2-diphenylethenyl, 2-(2-naphthyl)ethenyl and 4-phenyl-1,3-butadienyl;

d) $C_{2-6}$ alkenyl groups or 9-fluorenyl-$C_{1-6}$ alkyl group substituted with 1 to 3 naphthyl groups);

e) aliphatic hydrocarbon group as defined above substituted with the above-mentioned alicyclic hydrocarbon groups as defined above such as $C_{1-6}$ alkyl groups substituted with 1 to 3 $C_{3-12}$ cycloalkyl groups such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl; $C_{2-6}$ alkenyl groups substituted with 1 to 3 $C_{3-12}$ cycloalkyl groups; $C_{1-6}$ alkyl groups substituted with 1 to 3 $C_{5-10}$ cycloalkenyl groups; and $C_{2-6}$ alkenyl groups substituted with 1 to 3 $C_{5-10}$ cycloalkenyl groups;

f) $C_{1-6}$ aliphatic hydrocarbon group substituted with 1 to 3 (preferably 1 or 2) of the above-mentioned aromatic heterocyclic groups (for example, $C_{1-6}$ alkyl group and $C_{2-6}$ alkenyl group);

g) aliphatic hydrocarbon group substituted with an aromatic heterocyclic group include $C_{1-6}$ alkyl group with 1 to 3 of, for example, furyl group, thienyl group, imidazolyl group or pyridyl group (e.g. (2-furyl)methyl, thienylmethyl and 2-(1-imidazolyl)ethyl), and $C_{2-6}$ alkenyl group substituted with 1 to 3 of furyl group, thienyl group, imidazolyl group or pyridyl group;

h) $C_{6-14}$ aromatic hydrocarbon groups substituted with a $C_{1-3}$ alkyl group, a $C_{1-3}$ alkoxy group, halogen, nitro group, hydroxyl group or amino group, which are exemplified, more specifically, by phenoxy and 4-chlorophenoxy;

i) $C_{1-6}$ alkoxy groups ($R^7O$—), $C_{1-6}$ alkylthio groups ($R^7S(O)_x$—) and substituted $C_{1-6}$ alkyl groups substituted with 1 to 3 substituents selected from halogen atoms (e.g. fluorine, chlorine, bromine and iodine), hydroxyl group and $C_{1-6}$ alkoxy groups;

j) regarding $C_{1-6}$ alkoxy groups, mention is made of, for example, trifluoromethoxy, difluoromethoxy, 2,2,2-trifluoroethoxy and 1,1-difluoroethoxy;

k) $C_{6-14}$ arylthio groups ($R^7S(O)_x$—) optionally substituted with a $C_{1-3}$ alkyl group, a $C_{1-3}$ alkoxy group, halogen, nitro group, hydroxyl group or amino group, examples are phenylthio, naphthylthio and 4-chlorophenylthio;

l) alkylthio groups ($R^7S(O)_x$—) substituted by a aromatic heterocyclic group as defined above are pyridyl-$C_{1-6}$ alkylthio groups (e.g. 2-pyridylmethylthio and 4-pyridylmethylthio);

m) further examples of substituted $C_{1-6}$ alkylthio groups ($R^7S(O)_x$—) are trifluoromethyl-sulfanyl, difluoromethylsulfanyl, 2,2,2-trifluoroethylsulfanyl, 1,1-difluoroethylsulfanyl, trifluoromethylsulfinyl, difluoromethylsulfinyl, trifluoromethylsulfonyl and difluoromethylsulfonyl;

n) substituted alkyloxy carbonyl groups ($R^7OC(O)$—) are aralkyloxy carbonyl groups or heteroarylalkyloxycarbonyl groups wherein heteroaryloxy is an aromatic heterocyclic group as defined above such as phenyl-$C_{2-7}$ alkoxycarbonyl (e.g. benzyloxycarbonyl), naphthyl-$C_{2-7}$ alkoxycarbonyl, pyridyl-$C_{2-7}$ alkoxycarbonyl groups (e.g. 2-pyridylmethoxycarbonyl and 3-pyridylmethoxycarbonyl).

The ring A may optionally have 1 to 4 (preferably one or two) substituents at any substitutable position; such substituents are as defined above for the "aromatic azole ring".

The "arylvinyl" group can be present in the E-configuration or in the Z-configuration.

The ring A forms, depending on the kind of Y (CH or N), an optionally substituted benzene ring or an optionally substituted pyridine ring. As preferable examples, mention is made of an optionally substituted benzene ring. More preferable examples include a benzene ring optionally substituted with 1 or 2 $C_{1-6}$ alkoxy groups or a pyridine ring. Preferable examples of the ring A

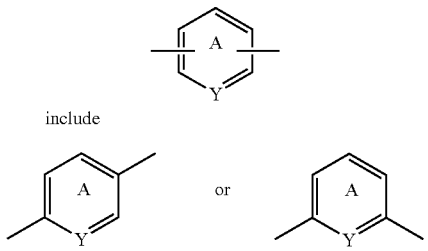

include and most preferable ones are a 1,3-phenylene group, or a 1,4-phenylene group or a pyridine-2,5-diyl group.

X denotes an oxygen atom (O), an optionally oxidized sulfur atom [$S(O)_x$ (x denotes an integer of 0 to 2)], or an optionally substituted nitrogen atom (NH or $NR^4$, $R^4$ denoting a substituent as defined above).

When the symbol X denotes an optionally substituted nitrogen atom, said substituent $R^4$ may be selected from $C_{1-6}$ alkyl, preferably methyl or ethyl.

Symbol n denotes an integer of 0 to 10, preferably 0 to 6, more preferably 1 to 3.

Symbol m denotes an integer of 1 to 5, preferably 1.

As salts of the compounds (I) of this invention, pharmaceutically acceptable ones are preferable, as exemplified by salts of inorganic bases, salts of organic bases, salts of inorganic acids, salts of organic acids, and salts of basic or acidic amino acids. Preferable examples of salts with inorganic bases include alkaline metal salts such as sodium salt and potassium salt; alkaline earth metal salts such as calcium salt and magnesium salt; and aluminum salt and ammonium salt. Preferable examples of salts with organic bases include salts with trimethylamine, triethylamine, pyridine, picoline, ethanolamine, diethanolamine, triethanolamine, dicyclohexylamine and N,N-dibenzylethylenediamine. Preferable examples of salts with inorganic acids include salts with hydrochloric acid, hydrobromic acid, nitric acid and phosphoric acid. Preferable examples of salts with organic acids include salts with formic acid, acetic acid, trifluoroacetic acid, fumaric acid, oxalic acid, tartaric acid, maleic acid, malonic acid, citric acid, succinic acid, malic acid, methanesulfonic acid, ethanesulfonic acid, benzenesulfonic acid, naphthalenesulfonic acid and p-toluenesulfonic acid. Preferable examples of salts with basic amino acids include salts with arginine, lysine and ornithine. Preferable examples of salts with acidic amino acids include salts with aspartic acid and glutamic acid. The compound (I) of this invention or salts thereof may optionally be used as hydrates.

A preferred embodiment of the present invention are the compounds of formula I-1

(formula I-1)

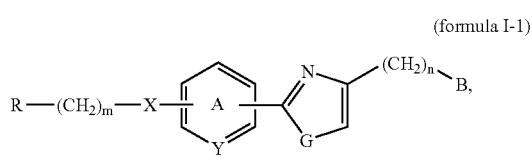

wherein
G denotes —O— or —S—;
X, Y and the cyclic group B are defined as above;
m and n are each 1; and R, denotes a group of formula

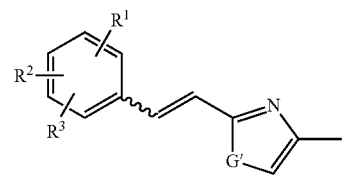

wherein
$R^1$, $R^2$, $R^3$, G' are defined as above.

Still another embodiment of the present invention are compounds of formula (I-2)

formula (I-2)

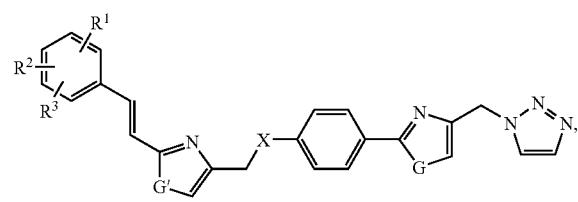

wherein
$R^1$ is halogen;
—O-alkyl;
—S-alkyl; —S(O)-alkyl; —S(O)$_2$-alkyl;
—N-alkyl;
—SF$_5$; or alkyl, all alkyl groups being optionally once or several times substituted by halogen;
$R^2$ is hydrogen; or
halogen; and
$R^3$ is hydrogen; or
$R^1$ and $R^2$ together with the carbon atoms to which they are attached form a 5 or 6 membered heterocyclic ring; and
$R^3$ is hydrogen; or
halogen;

X, G and G' have the significance given above; and their pharmaceutically acceptable salts.

Still another embodiment of the present invention are compounds of formula I or I-2 wherein
$R^1$ is halogen;
—O-alkyl;
—S-alkyl; —S(O)-alkyl; —S(O)$_2$-alkyl;
—N-alkyl;
—SF$_5$; or alkyl, all alkyl groups being optionally once or several times substituted by halogen;
$R^2$ is hydrogen; or
halogen;
$R^3$ is hydrogen;
X is —S—; —N(CH$_3$)— or —NH—; and
G' and G are —O—;

or alternatively
X and G are —O—; and
G' is —S—; and their pharmaceutically acceptable salts.

Such a compound is for example:

1-[2-(4-{2-[(E)-2-(4-Trifluoromethyl-phenyl)-vinyl]-thiazol-4-ylmethoxy}-phenyl) -oxazal-4-ylmethyl]-1H-[1,2,3]triazole.

Still another embodiment of the present invention are compounds of formula I or I-2 wherein
$R^1$ is halogen;
—O-alkyl;
—S-alkyl; —S(O)-alkyl; —S(O)$_2$-alkyl;
—N-alkyl;
—SF$_5$; or alkyl, all alkyl groups being optionally once or several times substituted by halogen;
$R^2$ is hydrogen; or
halogen;
$R^3$ is hydrogen;
X, G' and G are all —O—; and their pharmaceutically acceptable salts.

Such compounds are for example:

1-[2-(4-{2-[(E)-2-(4-Trifluoromethyl-phenyl)-vinyl]-oxazol-4-ylmethoxy}-phenyl) -oxazol-4-ylmethyl]-1H-[1,2,3]triazole, 1-[2-(4-{2-[(E)-2-(4-Trifluoromethoxy-phenyl)-vinyl]-oxazol-4-ylmethoxy}-phenyl) -oxazol-4-ylmethyl]-1H-[1,2,3]triazole, 1-[2-(4-{2-[(E)-2-(4-Trifluoromethylsulfanyl-phenyl)-vinyl]-oxazol-4-ylmethoxy}-phenyl)-oxazol-4-ylmethyl]-1H-[1,2,3]triazole, 1-[2-(4-{2-[(E)-2-(4-Methoxy-phenyl)-vinyl]-oxazol-4-ylmethoxy}-phenyl)-oxazol-4-ylmethyl]-1H-[1,2,3]triazole, 1-[2-(4-{2-[(E)-2-(4-Chloro-phenyl)-vinyl]-oxazol-4-ylmethoxy}-phenyl)-oxazol-4-ylmethyl]-1H-[1,2,3]triazole, 1-[2-(4-{2-[(E)-2-(-4-Trifluoromethylsulfinyl-phenyl)-vinyl]-oxazol-4-ylmethoxy}-phenyl)-oxazol-4-ylmethyl]-1H-[1,2,3]triazole, or 1-[2-(4-{2-[(E)-2-(4-Pentafluorosulfanyl-phenyl)-vinyl]-oxazol-4-ylmethoxy}-phenyl) -oxazol-4-ylmethyl]-1H-[1,2,3]triazole.

Still another embodiment of the present invention are compounds of formula I or I-2, wherein
$R^1$ is halogen;
—O-alkyl;
—S-alkyl; —S(O)-alkyl; —S(O)$_2$-alkyl;
—N-alkyl;
—SF$_5$; or alkyl, all alkyl groups being optionally once or several times substituted by halogen;
$R^2$ is hydrogen; or
halogen;
$R^3$ is hydrogen;
G is —S—;
G' is —S— or —O—; and
X is —O—; —NH— or —N(CH$_3$)—; and their pharmaceutically acceptable salts.

Such compounds are for example:

1-[2-(4-{2-[(E)-2-(4-Trifluoromethyl-phenyl)-vinyl]-oxazol-4-ylmethoxy}-phenyl) -thiazol-4-ylmethyl]-1H-[1,2,3]triazole, or 1-[2-(4-{2-[(E)-2-(4-Trifluoromethyl-phenyl)-vinyl]-thiazol-4-ylmethoxy}-phenyl) -thiazol-4-ylmethyl]-1H-[1,2,3]triazole.

Still another embodiment of the present invention are compounds of formula (I-3)

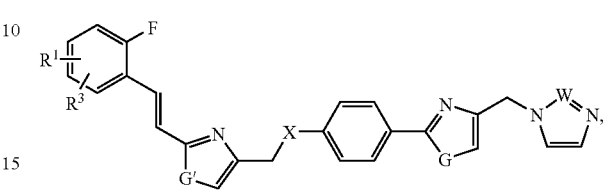

formula (I-3)

wherein
$R^1$ is halogen;
—O-alkyl;
—S-alkyl; —S(O)-alkyl; —S(O)$_2$-alkyl;
—N-alkyl;
—SF$_5$; or
alkyl, all alkyl groups being optionally once or several times substituted by halogen; and
$R^3$ is hydrogen;
W is —N═; or
—C($R^8$)═; wherein
$R^8$ is hydrogen or $C_{1-6}$ alkyl, which is once or several times substituted by hydroxy;
X is —O—; —S—; —S(O)—; —S(O)$_2$—; —NH— or —N(CH$_3$)—; and
G' and G are independently —O— or —S—; and their pharmaceutically acceptable salts.

Such compounds are for example:

2-[(E)-2-(2-Fluoro-4-trifluoromethyl-phenyl)-vinyl]-4-[4-(4-imidazol-1-ylmethyl -thiazol-2-yl)-phenoxymethyl]-oxazole, 2-[(E)-2-(2-Fluoro-4-trifluoromethyl-phenyl)-vinyl]-4-[4-(4-imidazol-1-ylmethyl -oxazol-2-yl)-phenoxymethyl]-oxazole, 2-[(E)-2-(2-Fluoro-4-chloro-phenyl)-vinyl]-4-[4-(4-imidazol-1-ylmethyl-oxazol-2yl)phenoxymethyl]-oxazole, 1-[2-(4-{2-[(E)-2-(2-Fluoro-4-trifluoromethyl-phenyl)-vinyl]-oxazol-4-ylmethoxy}-phenyl)-oxazol-4-ylmethyl]-1H-[1,2,3]triazole, 1-[2-(4-{2-[(E)-2-(4-Chloro-2-fluoro-phenyl)-vinyl]-oxazol-4-ylmethoxy}-phenyl) -oxazol-4-ylmethyl]-1H-[1,2,3]triazole, 1-[2-(4-{2-[(E)-2-(2-Fluoro-4-trifluoromethyl-phenyl)-vinyl]-oxazol-4-ylmethoxy}-phenyl)-thiazol-4-ylmethyl]-1H-[1,2,3]triazole, or 2-{1-[2-(4-{2-[(E)-2-(4-Chloro-2-fluoro-phenyl)-vinyl]-oxazol-4-ylmethoxy }-phenyl)-oxazol-4-ylmethyl]-1H-imidazol-2-yl}-ethanol.

Still another embodiment of the present invention are compounds of formula (I-4)

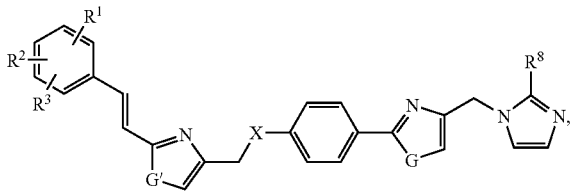

formula (I-4)

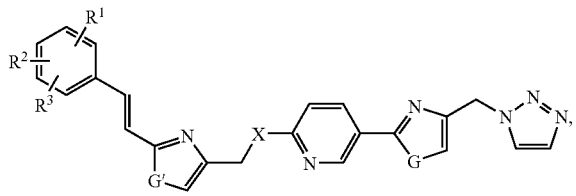

formula (I-5)

wherein
R$^1$ is halogen;
—O-alkyl;
—S-alkyl; —S(O)-alkyl; —S(O)$_2$-alkyl;
—N-alkyl;
—SF$_5$; or alkyl, all alkyl groups being optionally once or several times substituted by halogen;
R$^2$ is hydrogen; or
halogen; and
R$^3$ is hydrogen; or
R$^1$ and R$^2$ together with the carbon atoms to which they are attached form a 5 or 6 membered heterocyclic ring; and
R$^3$ is hydrogen; or
halogen;
R$^8$ is hydrogen; or
C$_{1-6}$ alkyl, which is once or several times substituted by hydroxy;
X, G' and G have the significance given herein before; and their pharmaceutically acceptable salts.

Still another embodiment of the present invention are compounds of formula I or I-4, wherein
R$^1$ is halogen;
—O-alkyl;
—S-alkyl; —S(O)-alkyl; —S(O)$_2$-alkyl
—N-alkyl;
—SF$_5$; or
alkyl, all alkyl groups being optionally once or several times substituted by halogen;
R$^2$ is hydrogen; or
halogen;
R$^3$ is hydrogen;
G' and G are independently —O— or —S—; and
X is —O—; —NH— or —N(CH$_3$)—; and their pharmaceutically acceptable salts.

Such compounds are for example:
1-[2-(4-{2-[(E)-2-(-4-Trifluoromethylsulfanyl-phenyl)-vinyl]-oxazol-4-ylmethoxy}-phenyl)-oxazol-4-ylmethyl]-1H-imidazole, or
1-[2-(4-{2-[(E)-2-(-4-Trifluoromethylsulfinyl-phenyl)-vinyl]-oxazol-4-ylmethoxy}-phenyl)-oxazol-4-ylmethyl]-1H-imidazole.

Still another embodiment of the present invention are compounds of formula (I-5)

wherein
R$^1$ is halogen;
—O-alkyl;
—S-alkyl; —S(O)-alkyl; —S(O)$_2$-alkyl;
—N-alkyl;
—SF$_5$; or
alkyl, all alkyl groups being optionally once or several times substituted by halogen;
R$^2$ is hydrogen; or
halogen; and
R$^3$ is hydrogen; or
R$^1$ and R$^2$ together with the carbon atoms to which they are attached form a 5 or 6 membered heterocyclic ring; and
R$^3$ is hydrogen; or
halogen;
X, G' and G have the significance defined in formula I; and
their pharmaceutically acceptable salts.

Another embodiment of the invention is a process for the manufacture of the compounds of formula (I), wherein a compound of formula (II)

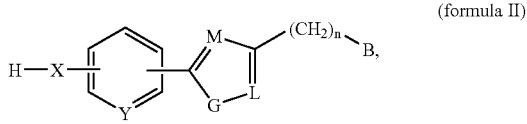

(formula II)

wherein B, X, Y, G, L, M and n have the meaning given herein before, is reacted with a compound of formula (III)

R—(CH$_2$)$_m$-E     (formula III), wherein R and m have the meanings given herein and E represents a suitable leaving group; and
if X stands for a group —NH—, a substituent (R$^4$) may optionally be introduced into said group to give a compound of formula (I) wherein R$^4$ is C$_{1-6}$ alkyl, which is optionally substituted once or several times with hydroxy; and
if X stands for a sulfur atom, said sulfur is optionally oxidized to give a sulfoxide or sulfone group; and
said compound of formula (I) is isolated from its reaction mixture; and
if desired, converted into a pharmaceutically acceptable salt.

The compounds of the general formula (I), or a pharmaceutically acceptable salt thereof, may be prepared by any process known to be applicable for the preparation of chemically-related compounds by the one skilled in the art. Such processes, when used to prepare the compounds of formula (I), or a pharmaceutically-acceptable salt thereof, are provided as a further feature of the invention and are illustrated by the following schemes 1, 2 and 3, in which, unless otherwise stated, the symbols have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

Compounds of formula (II) are new and are also subject of this invention.

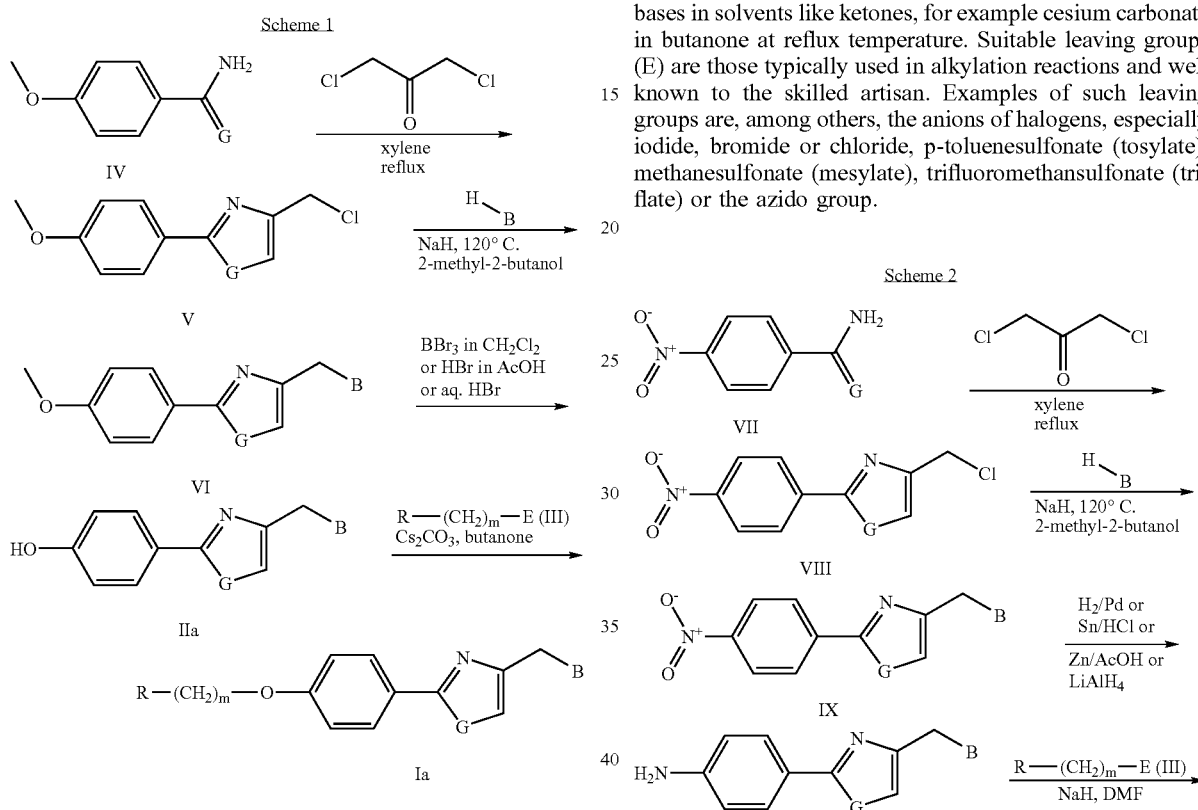

wherein the residue R stands for the group of formula

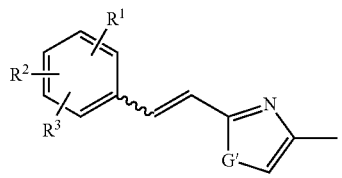

A preferred method for the synthesis of compounds of formula (I) where X denotes oxygen starts from O-protected oxybenzamides or oxybenzothioamides, e.g. (IV), wherein G denotes oxygen or sulfur. Condensation with 1,3-dichloroacetone yields the compound of formula (V). Typical solvents for reactions of this kind are xylene, toluene, benzene, acetone and chloroform. If desired the reaction can be carried out under solvent free conditions. The reaction temperatures may vary from 50° C. to 200° C. Alkylation of a group

H—B with compound (V) under basic conditions leads to intermediates of formula (VI) that can be deprotected by commonly known methods as indicated in scheme 1 to yield the phenolic compound (IIa). In the last step in scheme 1, the derivatives of formula (Ia) can be obtained by reactions well known to someone skilled in the art, e.g. by alkylation of the phenyls of formula (IIa) with compounds of formula (III). Typically the alkylation may be carried out in solvents like N,N-dimethylformamide, methanol, ethanol and isopropanol. Typical bases for this reaction are sodium methylate, sodium hydride or lithium diisopropyl amide. The reaction temperatures may vary from 50° C. to 150° C. Preferred alkylation procedures make use of alkaline carbonates as bases in solvents like ketones, for example cesium carbonate in butanone at reflux temperature. Suitable leaving groups (E) are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

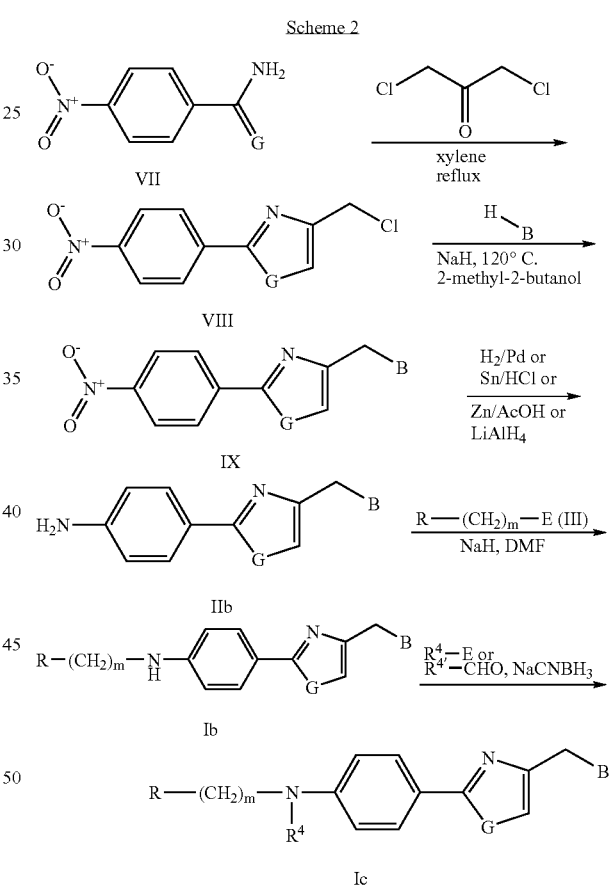

A preferred method for the synthesis of compounds of formula (I) where X denotes nitrogen starts from nitrated benzamides or benzothioamides, e.g. (VII), wherein G denotes oxygen or sulfur. Condensation with 1,3-dichloroacetone yields the compound of formula (VIII). Typical solvents for reactions of this kind are xylene, toluene, benzene, acetone and chloroform. If desired the reaction can be carried out under solvent free conditions. The reaction temperatures may vary from 50° C. to 200° C. Alkylation of a group

H—B with compound (VIII) under basic conditions leads to intermediates of formula (IX) that can be reduced by commonly known methods as indicated in scheme 2 to yield the amino compound (IIb). In the next step in scheme 2, the derivatives of formula (Ib) can be obtained by reactions well known to someone skilled in the art, e.g. by alkylation of the amines of formula (IIb) with compounds of formula (III). Typically the alkylation may be carried out in solvents like N,N-dimethylformamide, methanol, ethanol and isopropanol. Typical bases for this reaction are sodium methylate, sodium hydride or lithium diisopropyl amide. The reaction temperatures may vary from 50° C. to 150° C. If X stands for a substituted nitrogen ($NR^4$), the substituent may be introduced in a subsequent step by i) alkylation of the compound of formula (Ib) with a compound $R^4$-E, wherein $R^4$ and E have the meaning as defined hereinbefore, applying conditions as described above for alkylations, or ii) reacting (Ib) with an aldheyde $R^{4'}$—CHO, wherein $R^{4'}$ means a residue as described for $R^4$ but shortened by one terminal $CH_2$ group, under conditions of reductive amination to yield compounds of formula (Ic). The reaction is typically achieved in solvents like acetonitrile, N,N-dimethylformamide, methanol or ethanol and at temperatures between 20° C. and 150° C. Reducing agents typically employed are e.g. sodium cyanoborohydride ($NaCNBH_3$), sodium borohydride ($NaBH_4$) or lithium aluminium hydride ($LiAlH_4$).

An alternative route to compounds of formula (VIII) is the introduction of a nitro group into non-nitrated derivatives of this compound. This may be achieved by standard procedures for someone skilled in the art, e.g. by nitration in a mixture of sulfuric and nitric acid.

A preferred method for the synthesis of compounds of formula (I) where X denotes an optionally oxidized sulfur starts with an amino compound of formula (IIb). Diazotization in aqueous acid at 0-5° C. leads to the diazonium salt (X) that is reacted with a warm aqueous solution of ethyl potassium xanthogenate to form the substituted aryl xanthogenate that is saponified in situ to yield the thiol of formula (XI). Alkylation with compound (III) may be performed as described in scheme 1. If desired, the compound (Id) may be oxidized to the sulfoxide with agents like peracids, e.g. 3-chloro-benzenecarboperoxoic acid in dichloromethane or 2-iodoxybenzoic acid in chloroform or iodosobenzene in toluene to yield compound (Ie). Oxidation of compounds (Id) to sulfones of type (If) requires more rigorous conditions, for example periodic acid in acetonitrile under catalysis of chromium(VI) oxide.

The compounds of the present invention and their pharmaceutically acceptable salts possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above.

The activity of the present compounds as HER-signalling pathway inhibitors is demonstrated by the following biological assay:

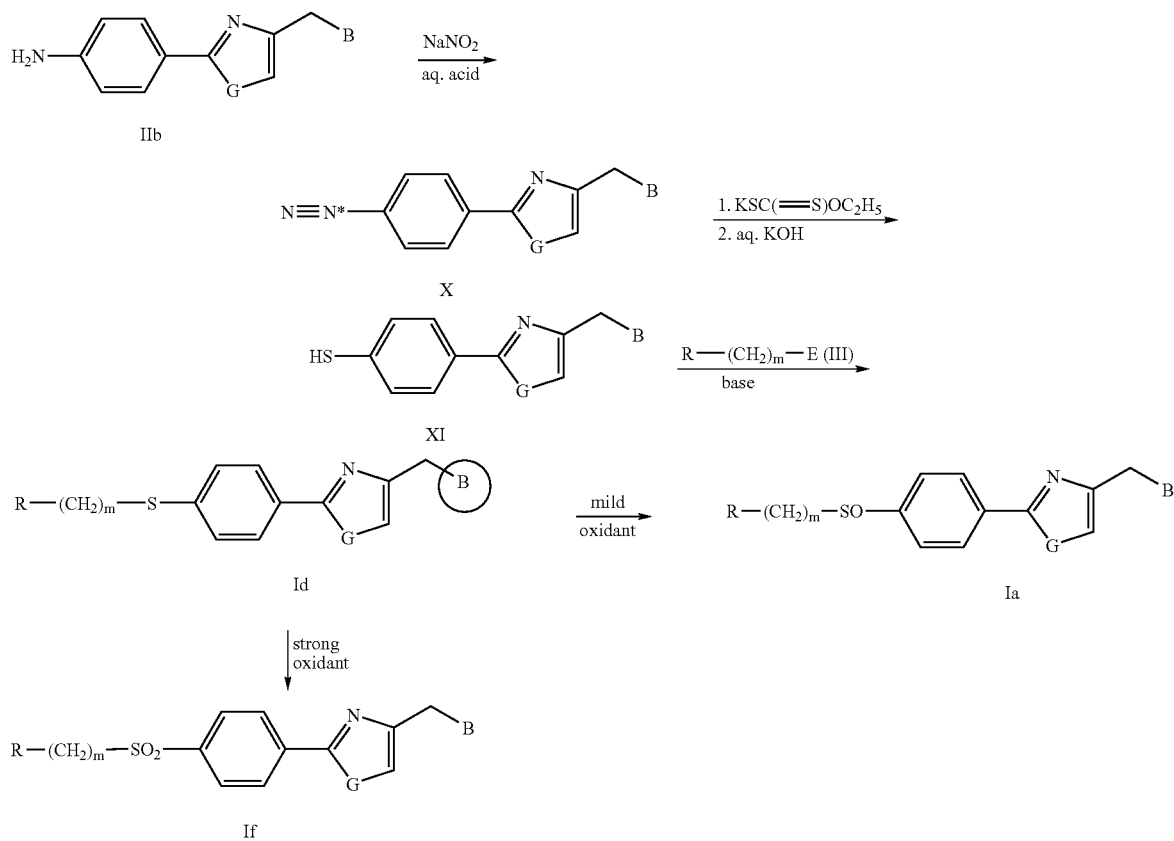

Assay Description:

A549 cells (human lung carcinoma cell line) were cultivated in RPMI 1640, 2.5% FCS, 2 mM glutamine, 100 u/ml Penicillin, 100 µg/ml Streptomycin. For the assay the cells were seeded in 384 well plates, 900 cells per well, in the same medium. The next day compounds (dissolved 10 mM in DMSO) were added in various concentrations ranging from 3 µM to 0.15 nM (10 concentrations, 1:3 diluted). After 5 days the MTT assay was done mainly according to the instructions of the manufacturer (Cell proliferation kit I, MTT, from Roche Molecular Biochemicals). In brief, MTT labeling reagent was added to a final concentration of 0.5 mg/ml, added and incubated for 4 hrs at 37 C, 5% CO2. During this incubation time purple formazan crystals are formed. After addition of the solubilization solution (20% SDS in 0.02 M HCl) the plates were incubated overnight at 37° C., 5% CO2.

After careful mixing the plates were measured in Victor 2 (scanning multiwell spectrophotometer, Wallac) at 550 nm.

A decrease in number of living cells results in a decrease in the total metabolic activity in the sample. The decrease directly correlates to the amount of purple color resulting from the solubilization of the purple formazan crystals.

Cells:
A549: 900 cells in 60 µl per well of 384 well plate (Greiner)
Medium: RPMI 1640, 2.5% FCS, glutamine, pen/strep.
Incubate 1 day at 37° C.
Induction:
  Dilution of compound in DMSO: 3 µl 10 mM+27 µl DMSO, dilute 1:3
  Add 2 µl of compound dilution row to 95 µl of medium
  Add 10 µl of compound dilution to 60 µl medium in test plate ➔0.3% DMSO per well
  Incubate 120 h (5 days) at 37° C., 5% $CO_2$
Analysis:
  Add 7 µl MTT (5 mg/ml/well), incubate 4 h at 37° C.
  Add 30 µl lysis buffer (20% SDS, 0.04 N HCl) per well
  Incubate overnight at 37° C.
Measurement:
Victor 2; 550 nm
Determination of $IC_{50}$ was done using XL-fit.
Results:

| Examples | IC$_{50}$ A549 [nM] |
|---|---|
| 2 | 46 |
| 3 | 46 |
| 4 | 45 |
| 5 | 69 |
| 6 | 7 |
| 7 | 37 |
| 8 | 70 |
| 9 | 11 |
| 10 | 60 |

The compounds according to this invention and their pharmaceutically acceptable salts can be used as medicaments, e.g. in the form of pharmaceutical compositions.

The pharmaceutical compositions can be administered orally, e.g. in the form of tablets, coated tablets, dragées, hard and soft gelatine capsules, solutions, emulsions or suspensions.

The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

Medicaments containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their HER-signalling pathway inhibition and their antiproliferative activity, said compounds are useful for the treatment of diseases such as cancer in humans or animals and for the production of corresponding medicaments. The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

EXAMPLE 1

1-[2-(4-{2-[(E)-2-(4-Methoxy-phenyl)-vinyl]-oxazol-4-ylmethoxy}-phenyl)-oxazol-4-ylmethyl]-1H-[1,2,3]triazole 15.12 g (100.0 mmol) 4-Methoxy-benzamide, 15.24 g (100 mmol) 1,3-dichloroacetone and 150 ml xylene were kept at reflux temperature for 24 h with continuous removal of water by use of a Dean-Stark trap. Another 15 g of 1,3-dichloroacetone were added and heating continued for additional 24 h. After removal of solvents in vacuo, the residue was triturated with isopropanol/water 1:1 and the crystals isolated and dried. Yield: 21.29 g (95%) 4-chloromethyl-2-(4-methoxy-phenyl)-oxazole as tan solid, melting at 80-82° C.

$^1$H-NMR(400 MHz, $D_6$-DMSO): δ=3.83(s, 3H, $OCH_3$), 4.72(s, 2H, $ClCH_2$), 7.08(d,2H, Ar—H), 7.91(d, 2H, Ar—H), 8.19(s, 1H, oxazole).

A suspension of 5.59 g (25 mmol) 4-chloromethyl-2-(4-methoxy-phenyl)-oxazole, 2.59 g (37.5 mmol) 1H-[1,2,3]triazole, 0.41 g (2.5 mmol) potassium iodide and 1.5 g (37.5 mmol) sodium hydroxide (NaOH) in 50 ml 2-methyl-2-butanol was stirred at 120° C. for 5 h. After evaporation, the residue was quenched with water and extracted with ethyl acetate. The extract was dried, concentrated and purified on silica. Elution with ethyl acetate yielded 4.1 g (64%) 1-[2-(4-methoxy-phenyl)-oxazol-4-ylmethyl]-1H-[1,2,3]triazole as white crystals, melting at 126-127° C.

MS: M=257.2(API+) $^1$H-NMR(400 MHz, $D_6$-DMSO): δ=3.82(s, 3H, $OCH_3$), 5.60(s, 2H, $CH_2$), 7.08(d, 2H, Ar—H), 7.76(s, 1H, triazole), 7.88(d, 2H, Ar—H), 8.18(s, 1H, triazole), 8.20(s, 1H, oaxzole).

A solution of 14.7 g (58.5 mmol) boron tribromide in 50 ml dichloromethane was dropped during 10 min to an ice-cold solution of 5.0 g (19.5 mmol) 1-[2-(4-methoxy-phenyl)-oxazol-4-ylmethyl]-1H-[1,2,3]triazole in 150 ml dichloromethane. The reaction mixture was stirred overnight at room temperature, cautiously poured on ice, the aqueous phase made basic with NaOH, washed with ethyl acetate and adjusted to pH 6.5 with 6 N hydrochloric acid (HCl). Extraction with ethyl acetate yielded 3.76 g (80%) 4-(4-[1,2,3]triazol-1-ylmethyl-oxazol-2-yl)-phenyl as white crystals, melting at 169-174° C.

MS: M=243.2(API+) $^1$H-NMR(400 MHz, $D_6$-DMSO): δ=5.58(s, 2H, $CH_2$), 6.88(d, 2H, Ar—H), 7.77(s, 1 H, triazole), 7.78(d, 2H, Ar—H), 8.16(2s, 2H, oxazole, triazole), 10.11(s, 1H, OH).

A mixture of 0.121 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.125 g (0.50 mmol) 4-chloromethyl-2-[2-(4-methoxy-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 182 mg raw material which was purified on silica. Elution with heptane/ethyl acetate 1:10 yielded 78 g (34%) 1-[2-(4-{2-[2-((E)-4-methoxy-phenyl)-vinyl]-oxazol-4-ylmethoxy}-phenyl)-oxazol-4-ylmethyl]-1H-[1,2,3]triazole as white crystals melting at 178° C.

MS: M=456.4(API+)

$^1$H-NMR(400 MHz, $D_6$-DMSO): δ=3.80(s, 3H, $OCH_3$), 5.09(s, 2H, $CH_2$), 5.60(2H, $CH_2$), 6.97(d, 2H, Ar—H), 7.00(d, 1H, =CH), 7.19(d, 2H, Ar—H), 7.48(d, 1H, =CH), 7.66(d, 2H, Ar—H), 7.76(s, 1H, triazole), 7.90(d, 2H, Ar—H), 8.19(3s, 3H, triazole, 2 oxazole).

EXAMPLE 2

1-[2-(4-{2-[(E)-2-(4-Trifluoromethoxy-phenyl)-vinyl]-oxazol-4-ylmethoxy}-phenyl)-oxazol-4-ylmethyl]-1H-[1,2,3]triazole A mixture of 0.121 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.152 g (0.50 mmol) 4-chloromethyl-2-[2-(4-trifluoromethoxy-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 249 mg(98%) 1-[2-(4-{2-[2-((E)-4-trifluoromethoxy-phenyl)-vinyl]-oxazol-4-ylmethoxy}-phenyl)-oxazol-4-ylmethyl]-1H-[1,2,3]triazole as light yellow crystals melting at 166-172° C.

MS: M=510.4(API+) $^1$H-NMR(400 MHz. $D_6$-DMSO): δ=5.11(s, 2H, $CH_2$), 5.60(s, 2H, $CH_2$), 7.19(d, 2H, Ar—H), 7.22(d, 1H, =CH), 7.40(d, 2H, Ar—H), 7.57(d, 1H, =CH), 7.75(s, 1H, triazole), 7.88 (dd, 4H, Ar—H), 8.17(s, 1H, triazole), 8.21(s, 1H, oxazole), 8.25(s, 1H, oxazole).

EXAMPLE 3

1-[2-(4-{2-[(E)-2-(-4-Trifluoromethylsulfanyl-phenyl)-vinyl]-oxazol-4-ylmethoxy}-phenyl)-oxazol-4-ylmethyl]-1H-[1,2,3]triazole A mixture of 0.121 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.160 g (0.50 mmol) 4-chloromethyl-2-[2-(4-trifluoromethylsulfanyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 253 mg(96%) 1-[2-(4-{2-[2-((E)-4-trifluoromethylsulfanyl-phenyl)-vinyl]-oxazol-4-ylmethoxy}-phenyl)-oxazol-4-ylmethyl]-1H-[1,2,3]triazole as light brown crystals melting at 172-173° C.

MS: M=526.4(API+) $^1$H-NMR(400 MHz, D$_6$-DMSO): δ=5.12(s, 2H, CH$_2$), 5.60(s, 2H, CH$_2$), 7.19(d, 2H, Ar—H), 7.31(d, 1H, =CH), 7.59(d, 1H, =CH), 7.74(d, 2H, Ar—H), 7.75(s, 1H, triazole), 7.89 (dd, 4H, Ar—H), 8.18(s, 1H, triazole), 8.21(s, 1H, oxazole), 8.28(s, 1H, oxazole).

EXAMPLE 4

1-[2-(4-{2-[(E)-2-(4-Trifluoromethyl-phenyl)-vinyl]-oxazol-4-ylmethoxy}-phenyl) -oxazol-4-ylmethyl]-1H-[1,2,3]triazole A mixture of 0.121 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.144 g (0.50 mmol) 4-chloromethyl-2-[2-(4-trifluoromethyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 220 mg raw material which was purified on silica. Elution with heptane/ethyl acetate 1:10 yielded 129 mg (52%) 1-[2-(4-{2-[2-((E)-4-trifluoromethyl-phenyl)-vinyl]-oxazol-4 -ylmethoxy}-phenyl)-oxazol-4-ylmethyl]-1H-[1,2,3]triazole as white crystals melting at 170° C.

MS: M=494.4(API+) $^1$H-NMR(400 MHz, D$_6$-DMSO): δ=5.12(s, 2H, CH$_2$), 5.60(s, 2H, CH$_2$), 7.19(d, 2H, Ar—H), 7.34(d, 1H, =CH), 7.62(d, 1H, =CH), 7.75(s, 1H, triazole), 7.76(d, 2H, Ar—H), 7.90 (d, 2H, Ar—H), 7.95(d, 2H, Ar—H), 8.17(s, 1H, triazole), 8.21(s, 1H, oxazole), 8.29(s, 1H, oxazole).

EXAMPLE 5

1-[2-(4-{2-[(E)-2-(4-Chloro-phenyl)-vinyl]-oxazol-4-ylmethoxy}-phenyl)-oxazol-4 -ylmethyl]-1H-[1,2,3]triazole A mixture of 0.121 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.127 g (0.50 mmol) 4-chloromethyl-2-[2-(4-chloro-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 82 mg raw material which was purified on silica. Elution with heptane/ethyl acetate 1:10 yielded 36 mg (16%) 1-[2-(4-{2-[2-((E)-4-chloro-phenyl)-vinyl]-oxazol-4-ylmethoxy}-phenyl)-oxazol-4 -ylmethyl]-1H-[1,2,3]triazole as white crystals melting at 208-210° C.

MS: M=460.3(API+) $^1$H-NMR(400 MHz, D$_6$-DMSO): δ=5.11(s, 2H, CH$_2$), 5.60(s, 2H, CH$_2$), 7.18(d, 2H,Ar—H), 7.20(d, 1H, =CH), 7.47(d, 2H, Ar—H), 7.53(d, 1H, =CH), 7.75(s, 1H, triazole), 7.76 (d, 2H, Ar—H), 7.90(d, 2H, Ar—H), 8.17(s, 1H, triazole), 8.21(s, 1H, oxazole), 8.25(s, 1H, oxazole).

EXAMPLE 6

1-[2-(4-{2-[(E)-2-(2-Fluoro-4-trifluoromethyl-phenyl)-vinyl]-oxazol-4-ylmethoxy}-phenyl)-oxazol-4-ylmethyl]-1H-[1,2,3]triazole A mixture of 73 mg (0.30 mmol) 4-(4-[1,2,3]triazol-1-ylmethyl-oxazol-2-yl)-phenol and 65 mg (0.20 mmol) cesium carbonate in 7 ml butanone was stirred at 60° C. for 30 min, then 92 mg (0.30 mmol) 4-chloromethyl-2-[2-(2-fluoro-4-trifluoromethyl -phenyl)-vinyl]-oxazole and 50 mg (0.30 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 160 mg raw material which was purified on silica. Elution with heptane/ethyl acetate 1:10 yielded 85 mg (55%) 1-[2-(4-{2-[2-((E)-2-fluoro-4-trifluoromethyl -phenyl)-vinyl]-oxazol-4-ylmethoxy}-phenyl)-oxazol-4-ylmethyl]-1H-[1,2,3]triazole as white crystals melting at 152-154° C.

MS: M=512.4(API+) $^1$H-NMR(400 MHz, D$_6$-DMSO): δ=5.13(s, 2H, CH$_2$), 5.60(s, 2H, CH$_2$), 7.19(d, 2H, Ar—H), 7.40(d, 1H, =CH), 7.60(d, 1H, =CH), 7.64(d, 1H, Ar—H), 7.76(s, 1H, triazole), 7.77 (d, 1H, Ar—H), 7.90(d, 2H, Ar—H), 8.16(m, 1H, Ar—H), 8.18(s, 1H, triazole), 8.21(s, 1H, oxazole), 8.31(s, 1H, oxazole).

EXAMPLE 7

1-[2-(4-{2-[(E)-2-(4-Trifluoromethyl-phenyl)-vinyl]-oxazol-4-ylmethoxy}-phenyl) -thiazol-4-ylmethyl]-1H-[1,2,3]triazole 13.38 g (80.0 mmol) 4-Methoxy-thiobenzamide, 15.23 g (120 mmol) 1,3-dichloroacetone and 400 ml acetone were stirred at room temperature for 3 days. The precipitate was isolated and dried, yielding 21.0 g (quant.) 4-methoxy-thiobenzimidic acid 3-chloro-2-oxo-propyl ester hydrochloride.

$^1$H-NMR(400 MHz, D$_6$-DMSO): δ=3.50(d, 1H, SCH$_2$), 3.81(d, 1H, SCH$_2$), 3.87 (s, 3H, OCH$_3$), 4.00(t, 2H, ClCH$_2$), 7.13(d, 2H, Ar—H), 7.97(d, 2H, Ar—H), 9.26(br, 1H, NH). 200° C. for 15 min. The solidified melt was triturated with ethyl acetate, filtered and dried to yield 18.33 g (95% overall) 4-chloromethyl-2-(4-methoxy-phenyl)-thiazole as light brown solid, melting at 125-128° C.

$^1$H-NMR(400 MHz, D$_6$-DMSO): δ=3.83(s, 3H, OCH$_3$), 4.85(s, 2H, CH$_2$), 7.03( d, 2H, Ar—H), 7.72(s, 1H, thiazole), 7.89(d, 2H, Ar—H), A suspension of 1.50 g (6.3 mmol) 4-chloromethyl-2-(4-methoxy-phenyl)-thiazole, 0.65 g (9.4 mmol) 1H-[1,2,3]triazole, 0.11 g (0.63 mmol) potassium iodide and 0.37 g (9.4 mmol) sodium hydroxide in 20 ml 2-methyl-2-butanol was stirred at 120° C. for 5 h. After evaporation, the residue was quenched with water and extracted with ethyl acetate. The extract was dried and concentrated to yield 1.4 g (82%) 1-[2-(4-methoxy-phenyl)-thiazol-4-ylmethyl]-1H-[1,2,3]triazole as beige crystals, melting at 89-94° C.

MS: M=273.3(API+) $^1$H-NMR(400 MHz, D$_6$-DMSO): δ=3.82(s, 3H, OCH$_3$), 5.76(s, 2H, CH$_2$), 7.04(d, 2H, Ar—H), 7.56(s, 1H, triazole), 7.77(s, 1H, triazole), 7.85(d, 2H, Ar—H), 8.22(s, 1H, thiazole).

A solution of 1.36 g (5.0 mmol) 1-[2-(4-methoxy-phenyl)-thiazol-4-ylmethyl]-1H-[1,2,3]triazole in 100 ml 47% aqueous hydrobromic acid was stirred at 70° C. for 6 h. The reaction mixture was poured on ice, made basic with concentrated ammonia and extracted with ethyl acetate to yield 0.87 g raw product. This was purified on silica. Elution with ethyl acetate/heptane 1:1 furnished 287 mg (22%) 4-(4-[1,2,3]triazol-ylmethyl-thiazol-2-yl) -phenol as white crystals, melting at 164-166° C.

MS: M=259.2(API+) $^1$H-NMR(400 MHz, D$_6$-DMSO): δ=5.73(s, 2H, CH$_2$), 6.86(d, 2H, Ar—H), 7.51(s, 1H, triazole), 7.74(d, 2H, Ar—H), 7.76(s, 1H, triazole), 8.21(s, 1H, thiazole), 10.03(s, 1H, OH)

A mixture of 0.129 g (0.50 mmol) 4-(4-[1,2,3]triazol-1-ylmethyl-thiazol-2-yl)-phenol and 0.10 g (0.30 mmol) cesium carbonate in 10 ml butanone was stirred at 60° C. for 30 min, then 0.144 g (0.50 mmol) 4-chloromethyl-2-[2-(4-trifluoromethyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 248 mg raw material which was purified on silica. Elution with ethyl acetate yielded 122 mg white crystals that gave, after recrystallisation from 6 ml ethanol, 79 mg (31%) pure 1-[2-(4-{2-[2-((E)-4-trifluoromethyl-phenyl)-vinyl]-oxazol-4-ylmethoxy}-phenyl)-thiazol-4-ylmethyl]-1H-[1,2,3]triazole melting at 163-165° C.

MS: M=510.3(API+) $^1$H-NMR(400 MHz, D$_6$-DMSO): δ=5.12(s, 2H, CH$_2$), 5.75(s, 2H, CH$_2$), 7.16(d, 2H, Ar—H), 7.34(d, 1H, =CH), 7.57(s, 1H, triazole), 7.63(d, 1H, =CH), 7.77(m, 3H, 2Ar—H+tiazole), 7.86(d, 2H, Ar—H), 7.95(d, 2H, Ar—H), 8.22(s, 1H, thiazole), 8.29(s, 1H, oxazole).

EXAMPLE 8

1-[2-(4-{2-[(E)-2-(2-Fluoro-4-trifluoromethyl-phenyl)-vinyl]-oxazol-4-ylmethoxy}-phenyl)-thiazol-4-ylmethyl]-1H-[1,2,3]triazole A mixture of 0.129 g (0.50 mmol) 4-(4-[1,2,3]triazol-1-ylmethyl-thiazol-2-yl)-phenyl and 0.10 g (0.30 mmol) cesium carbonate in 10 ml butanone was stirred at 60° C. for 30 min, then 0.153 g (0.50 mmol) 4-chloromethyl-2-[2-(2-fluoro-4-trifluoromethyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 390 mg raw material which was purified on silica. Elution with ethyl acetate yielded 131 mg white crystals (50%) pure 1-[2-(4-{2-[(E)-2-(2-fluoro-4-trifluoromethyl-phenyl)-vinyl]-oxazol-4-ylmethoxy}-phenyl)-thiazol-4-ylmethyl]-1H-[1,2,3]triazole melting at 180-182° C.

MS: M=528.3(API+) $^1$H-NMR(400 MHz, D$_6$-DMSO): δ=5.13(s, 2H, CH$_2$), 5.75(s, 2H, CH$_2$), 7.16(d 2H, Ar—H), 7.40(d, 1H, =CH), 7.55(s, 1H, triazole), 7.60(d, 1H, =CH), 7.64(m, 1H, Ar—H), 7.77 (m, 2H, Ar—H+triazole), 7.86(d, 2H, Ar—H), 8.16(t, 1H, Ar—H), 8.22(s, 1H, thiazole), 8.31(s, 1H, oxazole).

EXAMPLE 9

1-[2-(4-{2-[(E)-2-(4-Chloro-2-fluoro-phenyl)-vinyl]-oxazol-4-ylmethoxy}-phenyl) oxazole-4-ylmethyl]-1H-[1,2,3]triazole A mixture of 0.182 g (0.75 mmol) 4-(4-[1,2,3]triazol-1-ylmethyl-oxazol-2-yl)-phenol and 0.15 g (0.45 mmol) cesium carbonate in 15 ml butanone was stirred at 60° C. for 30 min, then 0.204 g (0.75 mmol) 4-chloromethyl-2-[2-(4-chloro-2-fluoro-phenyl)-vinyl]-oxazole and 0.125 g (0.75 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 195 mg raw material which was purified on silica. Elution with ethyl acetate yielded 98 mg white crystals (27%) pure 1-[2-(4-{2-[(E)-2-(4-chloro-2-fluoro-phenyl)-vinyl]-oxazol-4 -ylmethoxy}-phenyl)-oxazol-4-ylmethyl]-1H-[1,2,3]triazole melting at 193-194° C.

MS: M=478.2(API+) $^1$H-NMR(400 MHz, D$_6$-DMSO): δ=5.12(s, 2H, CH$_2$), 5.60(s, 2H, CH$_2$), 7.19(d, 2H, Ar—H), 7.26(d, 1H, =CH), 7.37(d, 1H, Ar—H), 7.53(d, 1H, =CH), 7.54(m, 1H, Ar—H), 7.75s, 1H, triazole), 7.90(d, 2H, Ar—H), 7.96(m, 1H, Ar—H), 8.18(s, 1H, triazole), 8.21(s, 1H, oxazole), 8.27(s, 1H, oxazole).

EXAMPLE 10

1-[2-(4-{2-[(E)-2-(4-Trifluoromethyl-phenyl)-vinyl]-thiazol-4-ylmethoxy}-phenyl) -oxazol-4-ylmethyl]-1H-[1,2,3]triazole A mixture of 4.30 g (20 mmol) 3-(4-trifluoromethyl-phenyl)-acrylamide and 1.0 g (4.5 mmol) phosphorous pentasulfide in 250 ml dioxane was stirred under reflux for 90 min. After evaporation, the residue was purified on silica. Elution with ethyl acetate/heptane 1:1 yielded 2.30 g (50%) 3-(4-trifluoromethyl-phenyl)-acrylthioamide as yellow crystals melting at 167-170° C.

MS: M=232.0(API+) $^1$H-NMR(400 MHz, D$_6$-DMSO): δ=7.11(d, 1H, =CH), 7.68(d, 1H, =CH), 7.80(m, 4H, Ar—H), 9.37(s, 1H, NH), 9.70(s, 1H, NH).

2.30 g (9.95 mmol) 3-(4-Trifluoromethyl-phenyl)-acrylthioamide, 2.52 g (19.90 mmol) 1,3-dichloroacetone and 75 ml acetone were stirred at room temperature for 24 h. The precipitate was isolated and dried, yielding 2.50 g (70%) 3-(4-trifluoromethyl-phenyl)-thioacrylimidic acid 3-chloro-2-oxo-propyl ester hydrochloride.

MS: M=322.2(API+) $^1$H-NMR(400 MHz, D$_6$-DMSO): δ=3.32(d, 1H, SCH$_2$), 3.65(d, 1H, SCH$_2$), 3.85(t, 2H, ClCH$_2$), 7.29(d, 1H, =CH), 7.37(br, 2H, NH$_2$+), 7.44(d, 1H, =CH), 7.78(d, 2H,Ar—H), 7.96(d, 2H, Ar—H).

Cyclization was achieved by heating of 2.5 g of the aforementioned intermediate to 200° C. for 10 min. The solidified melt was triturated with ethyl acetate, filtered and dried to yield 2.1 g (69% overall) 4-chloromethyl-2-[2-(4-trifluoromethyl-phenyl)-vinyl]-thiazole as light red solid, melting at 93-95° C.

MS: M=304.1(API+) $^1$H-NMR(400 MHz, D$_6$-DMSO): δ=4.86(s, 2H, CH$_2$), 7.59(d, 1H, =CH), 7.68(d, 1H, =CH), 7.76(d, 2H, Ar—H), 7.79(s, 1H, thiazole), 7.94(d, 2H, Ar—H).

A mixture of 0.1212 g (0.50 mmol) 4-(4-[1,2,3]triazol-1-ylmethyl-oxazol-2-yl)-phenol and 0.10 g (0.30 mmol) cesium carbonate in 10 ml butanone was stirred at 60° C. for 30 min, then 0.152 g (0.50 mmol) 4-chloromethyl-2-[2-(4-trifluoromethyl-phenyl)-vinyl]-thiazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 201 mg raw material which was recrystallised from ethanol to yield 171 mg (67%) 1-[2-(4-{2-[(E)-2-(4-trifluoromethyl-phenyl)-vinyl]-thiazol-4-ylmethoxy}-phenyl)-oxazol-4-ylmethyl]-1H-[1,2,3] triazole as white crystals melting at 179-181° C.

MS: M=510.2(API+) $^1$H-NMR(400 MHz, D$_6$-DMSO): δ=5.28(s, 2H, CH$_2$), 5.60(s, 2H, CH$_2$), 7.21(d, 2H, Ar—H), 7.604(d, 1H, =CH), 7.69(d, 1H, =CH), 7.75(m, 4H), 7.92(m, 4H), 8.18(s, 1H, thIAZOLE), 8.21(s, 1H, oxazole).

EXAMPLE 11

1-[2-(4-{2-[(E)-2-(4-Trifluoromethyl-phenyl)-vinyl]-thiazol-4-ylmethoxy}-phenyl)-thiazole-4-ylmethyl]-1H-[1,2,3]triazole A mixture of 0.129 g (0.50 mmol) 4-(4-[1,2,3]triazol-1-ylmethyl-thiazol-2-yl)-phenol and 0.10 g (0.30 mmol) cesium carbonate in 10 ml butanone was stirred at 60° C. for 30 min, then 0.153 g (0.50 mmol) 4-chloromethyl-2-[2-(4-trifluoromethyl-phenyl)-vinyl]-thiazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 174 mg raw material which was purified on silica. Elution with ethyl acetate/heptane 5:1 yielded 86 mg white crystals (33%) of 1-[2-(4-{2-[2-((E)-4-trifluoromethyl-phenyl)-vinyl]-thiazol-4-ylmethoxy}-phenyl)-thiazol-4-ylmethyl]-1H-[1,2,3]triazole melting at 146-148° C.

MS: M=526.2(API+) $^1$H-NMR(400 MHz, D$_6$-DMSO): δ=5.27(s, 2H, CH$_2$), 5.75(s, 2H, CH$_2$), 7.17(d, 2H, Ar—H), 7.57(s, 1H, triazole), 7.60(d, 1H, =CH), 7.69(d, 1H, =CH), 7.77(m, 4H, 2Ar—H+thiazole+triazole), 7.87(d, 2H, Ar—H), 7.94(d, 2H, Ar—H), 8.22(s, 1H, thiazole).

EXAMPLE 12

2-[(E)-2-(2-Fluoro-4-trifluoromethyl-phenyl)-vinyl]-4-[4-(4-imidazol-1-ylmethyl-thiazole-2-yl)-phenoxymethyl]-oxazole A suspension of 2.40 g (10 mmol) 4-chloromethyl-2-(4-methoxy-phenyl)-thiazol, 1.02 g (15 mmol) imidazole, 0.17 g (1 mmol) potassium iodide and 0.60 g (15 mmol) sodium hydroxide in 25 ml 2-methyl-2-butanol was stirred at 120° C. for 5 h. After evaporation, the residue was quenched with water and extracted with ethyl acetate. The extract was dried and concentrated to yield 2.47 g (91%) 1-[2-(4-methoxy-phenyl)-thiazol-4-ylmethyl]-imidazole as beige crystals, melting at 89-90° C.

MS: M=272.2(API+) $^1$H-NMR(400 MHz, D$_6$-DMSO): δ=3.82(s, 3H, OCH$_3$), 5.32(s, 2H, CH$_2$), 6.92(s, 1H, imidazole), 7.05(d, 2H, Ar—H), 7.25(s, 1H, imidazole), 7.42(s, 1H, imidazole), 7.77(s, 1H, thiazole), 7.86(d, 2H, Ar—H).

A solution of 0.54 g (2.0 mmol) 1-[2-(4-methoxy-phenyl)-thiazol-4-ylmethyl]-imidazole in 15 ml 47% aqueous hydrobromic acid was stirred at 70° C. for 4 days. The reaction mixture was poured on ice, made basic with concentrated ammonia and extracted with ethyl acetate to yield 0.44 g (85%) raw 4-[4-(imidazol-1-ylmethyl)-thiazol-2-yl]-phenol as tan crystals.

MS: M=258.1(API+) $^1$H-NMR(400 MHz, D$_6$-DMSO): δ=5.31(s, 2H, CH$_2$), 6.86(d, 2H, Ar—H), 6.92(s, 1H, imidazole), 7.24(s, 1H, imidazole), 7.38(s, 1H, thiazole), 7.75 (d, 2H, Ar—H), 10.05(s, 1H, OH).

A mixture of 0.129 g (0.50 mmol) 4-[4-(imidazol-1-ylmethyl)-thiazol-2-yl]-phenol and 0.10 g (0.30 mmol) cesium carbonate in 10 ml butanone was stirred at 60° C. for 30 min, then 0.153 g (0.50 mmol) 4-chloromethyl-2-[2-(2-fluoro-4-trifluoromethyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 241 mg raw material which was purified on silica. Elution with ethyl acetate/methanol 5:1 yielded 88 mg (33%) 2-[(E)-2-(2-Fluoro-4-trifluoromethyl-phenyl)-vinyl]-4-[4-(4-imidazol-1-ylmethyl-thiazol-2-yl)-phenoxymethyl]-oxazole as off-white crystals melting at 133-135° C.

MS: M=527.3(API+) $^1$H-NMR(400 MHz, D$_6$-DMSO): δ=5.12(s, 2H, CH$_2$), 5.32(s, 2H, CH$_2$), 6.92(s, 1H, imidazole), 7.16(d, 2H, Ar—H), 7.25(s, 1H, imidazole), 7.40(m, 2H), 7.61(m, 2H), 7.77(d, 2H, Ar—H), 7.87(d, 2H, Ar—H), 8.16(s, 1H, thiazole), 8.31(s, 1H, oxazole).

EXAMPLE 13

2-[(E)-2-(2-Fluoro-4-trifluoromethyl-phenyl)-vinyl]-4-[4-(4-imidazol-1-ylmethyl-oxazol-2-yl)-phenoxymethyl]-oxazole A suspension of 2.23 g (10 mmol) 4-chloromethyl-2-(4-methoxy-phenyl)-oxazole, 1.02 g (15 mmol) imidazole, 0.17 g (1 mmol) potassium iodide and 0.60 g (15 mmol) sodium hydroxide in 25 ml 2-methyl-2-butanol was stirred at 120° C. for 5 h. After evaporation, the residue was quenched with water and extracted with ethyl acetate. The extract was dried and concentrated to yield 2.51 g (98%) 1-[2-(4-methoxy-phenyl)-oxazol-4-ylmethyl]-imidazole as beige crystals.

MS: M=256.2(API+) $^1$H-NMR(400 MHz, D$_6$-DMSO): δ=3.82(s, 3H, OCH$_3$), 5.16(s, 2H, CH$_2$), 6.91(s, 1H, imidazole), 7.08(d, 2H, Ar—H), 7.21(s, 1H, imidazole), 7.74(s, 1H, imidazole), 7.89(d, 2H, Ar—H), 8.09(s, 1H, oxazole).

A solution of 0.51 g (2.0 mmol) 1-[2-(4-methoxy-phenyl)-oxazol-4-ylmethyl]-imidazole in 15 ml 47% aqueous hydrobromic acid was stirred at 70° C. for 4 days. The reaction mixture was poured on ice, made basic with concentrated ammonia and extracted with ethyl acetate to yield 0.28 g (58%) raw 4-[4-(imidazol-1-ylmethyl)-oxazol-2-yl]-phenol as tan crystals.

MS: M=242.3(API+) $^1$H-NMR(400 MHz, D$_6$-DMSO): δ=5.14(s, 2H, CH$_2$), 6.88(m, 3H), 7.20(s, 1H, imidazole), 7.77(m, 3H), 8.05(s, 1H, oxazole), 10.10(s, 1H, OH).

A mixture of 0.121 g (0.50 mmol) 4-[4-(imidazol-1-ylmethyl)-oxazol-2-yl]-phenol and 0.10 g (0.30 mmol) cesium carbonate in 10 ml butanone was stirred at 60° C. for 30 min, then 0.153 g (0.50 mmol) 4-chloromethyl-2-[2-(2-fluoro-4-trifluoromethyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 221 mg raw material which was purified on silica. Elution with ethyl acetate/methanol 5:1 yielded 101 mg (40%) 2-[(E)-2-(2-fluoro-4-trifluoromethyl-phenyl)-vinyl]-4-[4-(4-imidazol-1-ylmethyl-oxazol-2-yl)-phenoxymethyl]-oxazole as off-white crystals melting at 150-153° C.

MS: M=511.2(API+) $^1$H-NMR(400 MHz, D$_6$-DMSO): δ=5.13(s, 2H, CH$_2$), 5.16(s, 2H, CH$_2$), 6.90(br, 1H, imidazole), 7.19(d, 2H, Ar—H), 7.20(s, 1H, imidazole), 7.40(d, 1H, =CH), 7.60(d, 1H, =CH), 7.64(d, 1H), 7.77(m, 2H), 7.90(d, 2H, Ar—H), 8.10(s, 1H, oxazole), 8.16(t, 1H, Ar—H), 8.31(s, 1H, oxazole).

EXAMPLE 14

2-[(E)-2-(2-Fluoro-4-chloro-phenyl)-vinyl]-4-[4-(4-imidazol-1-ylmethyl-oxazol-2-yl)phenoxymethyl]-oxazole A mixture of 0.121 g (0.50 mmol) 4-[4-(imidazol-1-ylmethyl)-oxazol-2-yl]-phenol and 0.10 g (0.30 mmol) cesium carbonate in 10 ml butanone was stirred at 60° C. for 30 min, then 0.136 g (0.50 mmol) 4-chloromethyl-2-[2-(2-fluoro-4-chloro-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 198 mg raw material which was purified on silica. Elution with ethyl acetate/methanol 5:1 yielded 111 mg (46%) 2-[(E)-2-(2-fluoro-4-chloro-phenyl)-vinyl]-4-[4-(4-imidazol-1-ylmethyl-2-yl)-phenoxymethyl]-oxazole as white crystals melting at 166-167° C.

MS: M=477.2(API+) $^1$H-NMR(400 MHz, D$_6$-DMSO): δ=5.12(s, 2H, CH$_2$), 5.16(s, 2H, CH$_2$), 6.91(s, 1H, imidazole), 7.19(d, 2H, Ar—H), 7.21(s, 1H, imidazole), 7.26(d, 1H, =CH), 7.36(d, 1H), 7.52(m, 2H), 7.74(s, 1H), 7.90(d, 2H, Ar—H), 7.94(t, 1H, Ar—H), 8.10(s, 1H, oxazole).

EXAMPLE 15

1-[2-(4-{2-[(E)-2-(–4-Trifluoromethylsulfinyl-phenyl)-vinyl]-oxazol-4-ylmethoxy}-phenyl)-oxazol-4-ylmethyl]-1H-[1,2,3]triazole A solution of 158 mg (0.30 mmol) 1-[2-(4-{2-[2-((E)-4-trifluoromethylsulfanyl -phenyl)vinyl]-oxazol-4-ylmethoxy}-phenyl)-oxazol-4-ylmethyl]-1H-[1,2,3]triazole and 75 mg (0.33 mmol) 3-chloro-benzenecarboperoxoic acid in dichloromethane was stirred at room temperature over night, then another 37 mg 3-chloro-benzenecarboperoxoic acid were added and stirring continued for another 8 hours. After evaporation, 15 ml sodium carbonate solution was added and the mixture extracted with two portions of 15 ml ethyl acetate. The combined organic layers were washed with water, dried over sodium sulfate and evaporated. After chromatography on silica and elution with ethyl acetate/heptane 10:1 resulted 34 mg (21%) 1-[2-(4-{2-[2-((E)-4-trifluoromethylsulfinyl-phenyl)-vinyl]-oxazol-4-ylmethoxy}-phenyl)-oxazol-4-ylmethyl]-1H-[1,2,3]triazole as off-white crystals melting at 167-169° C.

MS: M=542.0(API+) $^1$H-NMR(400 MHz, D$_6$-DMSO): δ=5.13(s, 2H, CH$_2$), 5.60(s, 2H, CH$_2$), 7.19(d, 2H, Ar—H), 7.39(d, 1H, =CH), 7.64(d, 1H, =CH), 7.76(s, 1H, triazole), 7.91(dd, 4H, Ar—H), 8.06(d, 2H, Ar—H), 8.18(s, 1H, triazole), 8.21(s, 1H, oxazole), 8.30(s, 1H, oxazole).

EXAMPLE 16

1-[2-(4-{2-[(E)-2-(–4-Trifluoromethylsulfanyl-phenyl)-vinyl]-oxazol-4-ylmethoxy}-phenyl)-oxazol-4-ylmethyl]-1H-imidazole A mixture of 0.121 g (0.50 mmol) 4-(4-imidazol-1-ylmethyl-oxazol-2-yl)-phenol and 0.10 g (0.30 mmol) cesium carbonate in 10 ml butanone was stirred at 60° C. for 30 min, then 0.160 g (0.50 mmol) 4-chloromethyl-2-[2-(4-trifluoromethylsulfanyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give 110 mg (42%) of the title compound as light brown crystals melting at 144-145° C. (from 2-propanol).

MS: M=525.2(API+) $^1$H-NMR(400 MHz, D$_6$-DMSO): δ=5.12(s, 2H, CH$_2$), 5.16(s, 2H, CH$_2$), 6.90 (s, 1H, imidazole), 7.19(d, 3H, 2Ar—H+imidazole), 7.31(d, 1H, =CH), 7.56(d, 1H, =CH), 7.74(d, 3H, 2Ar—H+imidazole), 7.86 (dd, 4H, Ar—H), 8.10(s, 1H, oxazole), 8.28(s, 1H, oxazole).

EXAMPLE 17

1-[2-(4-{2-[(E)-2-(–4-Trifluoromethylsulfinyl-phenyl)-vinyl]-oxazol-4-ylmethoxy}-phenyl)-oxazol-4-ylmethyl]-1H-imidazole A mixture of 0.121 g (0.50 mmol) 4-(4-imidazol-1-ylmethyl-oxazol-2-yl)-phenol and 0.10 g (0.30 mmol) cesium carbonate in 10 ml butanone was stirred at 60° C. for 30 min, then 0.168 g (0.50 mmol) 4-chloromethyl-2-[2-(4-trifluoromethylsulfinyl-phenyl)-vinyl]-oxazole and 0.083 g (0.50 mmol) potassium iodide were added and stirring at 60° C. continued over night. After evaporation, 15 ml water was added and the mixture extracted with two portions of 15 ml ethyl acetate. The combined organic layers were washed with 1N sodium hydroxide and water, dried over sodium sulfate and evaporated to give, after recrystallisation from 2-propanol, 121 mg (45%) of the title compound as light brown crystals melting at 134-136° C.

MS: M=541.2(API+) $^1$H-NMR(400 MHz, D$_6$-DMSO): δ=5.13(s, 2H, CH$_2$), 5.16(s, 2H, CH$_2$), 6.90 (s, 1H, imidazole), 7.19(d, 3H, 2Ar—H+imidazole), 7.40(d, 1H, =CH), 7.64(d, 1H, =CH), 7.73(s, 1H, imidazole), 7.90(dd, 4H, Ar—H), 8.06(d, 2H, Ar—H), 8.10(s, 1H, oxazole), 8.30(s, 1H, oaxazole

EXAMPLE 18

2-{1-[2-(4-{2-[(E)-2-(4-Chloro-2-fluoro-phenyl)-vinyl]-oxazol-4-ylmethoxy }-phenyl)-oxazole-4-ylmethyl]-1H-imidazol-2-yl}-ethanol i) 4-Benzyloxybenzamide To a suspension of 4.565 g (20 mmol) 4-benzyloxybenzoic acid in 25 ml THF and 0.3 ml N,N-dimethylformamide was added dropwise at 0° C. a solution of 2.6 ml oxalyl chloride in 5 ml THF. Stirring was continued for 3 hours at room temperature, then the suspension was added slowly to a stirred ice-cold solution of concentrated aqueous ammonia. The organic solvent was evaporated, 100 ml water added and the precipitate isolated and dried in vacuo at 50° C. Yield: 4.29 g (94%) white solid.

MS: M=228.0(API+) $^1$H-NMR(400 MHz, D$_6$-DMSO): δ=5.16(s, 2H, OCH$_2$), 7.05(d, 2H, Ar—H), 7.18(br, 1H, NH), 7.38(m, 3H, Ar—H), 7.46(d, 2H, Ar—H), 7.85(m, 3H, 2Ar—H+NH).

ii) 2-(4-Benzyloxy-phenyl)-4-chloromethyl-oxazole

A mixture of 4.2 g (18.5 mmol) 4-benzyloxybenzamide and 4.69 g (37 mmol) 1,3-dichloroacetone in 100 ml xylene was refluxed for 4 hours using a Dean-Stark trap. After evaporation, the residue was triturated with a mixture of 25 ml 2-propanol and 25 ml water and the precipitate isolated. After elution with ethyl acetate/heptane 3:1 from silica resulted 3.6 g (65%) off-white crystals of 2-(4-benzyloxy-phenyl)-4-chloromethyl-oxazole.

MS: M=300.0(API+) $^1$H-NMR(400 MHz, D$_6$-DMSO): δ=4.72(s, 2H, ClCH$_2$), 5.19(s, 2H, OCH$_2$), 7.17d, 2H, Ar—H), 7.36(d, 1H, Ar—H), 7.41(t, 2H, Ar—H), 7.48(d, 2H, Ar—H), 7.92(d, 2H, Ar—H), 8.20(s, 1H, oxazole).

iii) 2-{1-[2-(4-Benzyloxy-phenyl)-oxazol-4-ylmethyl]-1H-imidazol-2-yl}-ethanol

A mixture of 2.10 g (7.0 mmol) 2-(4-benzyloxy-phenyl)-4-chloromethyl-oxazole, 0.86 g (7.7 mmol) 2-(2-hydroxy-ethyl)-1H-imidazole, 1.28 g (7.7 mmol) potassium iodide and 0.31 g (7.7 mmol) sodium hydroxide in 30 ml 2-methyl-2-butanol was stirred under reflux over night. After evaporation, water was added and the residue extracted into ethyl acetate. The extract was dried, evaporated and purified on silica. Elution with ethyl acetate/methanolic ammonia 85:15 yielded 0.98 g (37%) 2-{1-[2-(4-benzyloxy-phenyl)-oxazol-4-ylmethyl]-1H-imidazol-2-yl}-ethanol as tan solid.

MS: M=376.0(API+) $^1$H-NMR(400 MHz, D$_6$-DMSO): δ=2.70(t, 2H, CCH$_2$), 3.75(t, 2H, HOCH$_2$), 4.80(t, 1H, OH), 5.11(s, 2H, NCH$_2$), 5.18(s, 2H, OCH$_2$), 6.78(s, 1H, triazole), 7.10(s, 1H, triazole), 7.16(d, 2H, Ar—H), 7.35(d, 1H, Ar—H), 7.40(t, 2H, Ar—H), 7.47(d, 2H, Ar—H), 7.88(d, 2H, Ar—H), 8.04(s, 1H, oxazole).

iv) 4-{4-[2-(2-Hydroxy-ethyl)-imidazol-1-ylmethyl]-oxazol-2-yl}-phenol

A solution of 0.90 g (2.39 mmol) 2-{1-[2-(4-benzyloxy-phenyl)-oxazol-4-ylmethyl]-1H-imidazol-2-yl}-ethanol in 60 ml THF was hydrogenated for 2 hours over 250 mg 10% Pd/C at ambient temperature and pressure. After filtration, the solvent was evaporated to leave 0.55 g (80%) 4-{4-[2-(2-hydroxy-ethyl)-imidazol-1-ylmethyl]-oxazol-2-yl}-phenyl as light yellow crystals.

MS: M=286.0(API+) $^1$H-NMR(400 MHz, D$_6$-DMSO): δ=2.90(t, 2H, CCH$_2$), 3.74(t, 2H, HOCH$_2$), 4.80(t, 1H, OH), 5.10(s, 2H, NCH$_2$), 6.78(s, 1H, triazole), 6.88(d, 2H, Ar—H), 7.10(s, 1H, triazole), 7.78(d, 2H, Ar—H), 7.99(s, 1H, oxazole), 10.13(br, 1H, OH).

v) 2-{1-[2-(4-{2-[(E)-2-(4-Chloro-2-fluoro-phenyl)-vinyl]-oxazol-4-ylmethoxy}-phenyl)-oxazole-4-ylmethyl]-1H-imidazol-2-yl}-ethanol A mixture of 0.20 g (0.74 mmol) 4-{4-[2-(2-hydroxy-ethyl)-imidazol-1-ylmethyl]-oxazol-2-yl}-phenyl and 0.143 g (0.44 mmol) cesium carbonate in 10 ml butanone was stirred at 60° C. for 30 min, then 0.21 g (0.74 mmol) 4-chloromethyl-2-[2-(4-chloro-2-fluoro-phenyl)-vinyl]-oxazole and 0.123 g (0.74 mmol) potassium iodide were added and stirring at 60° C. continued over night. After evaporation, 15 ml water was added and the mixture extracted with three portions of 15 ml ethyl acetate. The combined organic layers were washed with 1N sodium hydroxide and water, dried over sodium sulfate and evaporated. Purification on silica yielded, after elution with heptane/ethyl acetate 1:5, slight yellow raw material (165 mg) that was recrystallized from 2-propanol to give 76 mg (20%) pure title compound as white crystals melting at 170-172° C.

MS: M=521.0(ESI+) $^1$H-NMR(400 MHz, D$_6$-DMSO): δ=2.91(t, 2H, CCH$_2$), 3.74(q, 2H, HOCH$_2$), 4.79(t, 1H, OH), 5.12(s, 4H, OCH$_2$+NCH$_2$), 6.78(s, 1H, triazole), 7.10(s, 1H, triazole), 7.19(d, 2H, Ar—H), 7.26(d, 1H, vinyl), 7.37(d, 1H, Ar—H), 7.53(m,2H, vinyl+Ar—H), 7.89(d, 2H, Ar—H), 7.95(t, 1H, Ar—H), 8.05(s, 1H, oxazole), 8.28(s, 1H, oxazole).

EXAMPLE 19

1-[2-(4-{2-[(E)-2-(4-Pentafluorosulfanyl-phenyl)-vinyl]-oxazol-4-ylmethoxy}-phenyl) -oxazol-4-ylm-ethyl]-1H-[1,2,3]triazole i) 3-(4-Pentafluorosulfanyl-phenyl)-acrylic Acid A mixture of 5.40 g (23.3 mmol) 4-pentafluorosulfanyl-benzaldehyde, 2.42 g (23.3 mmol) malonic acid, 0.20 g (2.3 mmol) piperidine and 10.0 ml pyridine was kept at reflux temperature until carbon dioxide development ceased (4 h). The reaction mixture was poured into a solution of 100 ml ice and 60 ml 6N HCl. The precipitate was isolated, washed with water, then with n-heptane and dried in vacuum at 40° C. Yield: 5.73 g (90%) 3-(4-pentafluorosulfanyl-phenyl)-acrylic acid.

MS: M=273.2 (ESI−) $^1$H-NMR(400 MHz, D$_6$-DMSO): δ=6.69(d, J=15.8 Hz, 1H, 2-H), 7.65(d, J=15.8 Hz, 1H, 3-H), 7.92(s, 4H, Ar—SF$_5$), 12.7(br, 1H, COOH). $^{19}$F-NMR(376 MHz, D$_6$-DMSO): δ=63.5(d, 4F), 86.3(quintet, 1F).

ii) 3-(4-Pentafluorosulfanyl-phenyl)-acrylamide

To a suspension of 5.70 g (20.8 mmol) 3-(4-pentafluorosulfanyl-phenyl)-acrylic acid in 30 ml tetrahydrofuran and 0.21 ml N,N-dimethyl formamide a solution of 3.47 ml (27.4 mmol) oxalyl chloride in 5.0 ml tetrahydrofuran was added dropwise at 0° C. within 10 min. Stirring was continued at 0-5° C. for 30 min. and 3 h at room temperature thereafter. The resulting solution was cooled to 0-5° C. again and then added within 15 min. to mixture of 300 ml ice and 120 ml of a 25% aqueous ammonia solution. The precipitated amide was collected, washed with water and n-heptane and dried at 40° C. in vacuo. Yield 5.17 g (91%) 3-(4-pentafluorosulfa-nyl-phenyl)-acrylamide.

MS: M=274.2(ESI+), 272.2(ESI−) $^1$H-NMR(400 MHz, D$_6$-DMSO): δ=6.76(d, J=15.8 Hz, 1H, 2-H), 7.26(s, br, 1H, NH), 7.48(d, J=15.8 Hz, 1H, 3-H), 7.66(br, 1H, NH), 7.78(d, 2H, Ar—SF$_5$), 7.93(d, 2H, ArSF$_{5)}$. $^{19}$F-NMR(376MHz, D$_6$-DMSO): δ=63.7(d, 4F), 86.8(quintet, 1F).

iii) 4-Chloromethyl-2-[2-(4-pentafluorosulfanyl-phenyl)-vi-nyl]-oxazole 4.10 g (15.0 mmol) 3-(4-Pentafluorosulfanyl-phenyl)-acrylamide, 2.37 g (18.7 mmol) dichloro acetone and 25.0 ml toluene were kept at reflux temperature for 12 h with continuous removal of water by use of a Dean-Stark trap. The reaction mixture was evaporated and purified by chromatography on silica gel (eluent: heptane/ethyl acetate 5:1). All fractions containing the product were evaporated and the residue stirred with 10 ml isohexane, the crystallized material isolated by filtration dried. Yield: 4.40 g (85%) 4-Chloromethyl-2-[2-(4-pentafluorosulfanyl-phenyl)-vinyl]-oxazole.

MS: M=346.1(APCI+), 344.2(APCI−). $^1$H-NMR(400 MHz D$_6$-DMSO): δ=4.72(s, 2H, CH$_2$Cl), 7.35(d, 1H, =CH), 7.62(d, 1H, =CH), 7.94(m, 4H, Ar—H), 8.23(s, 1H, oxazole).

iv) 1-[2-(4-{2-[(E)-2-(4-Pentafluorosulfanyl-phenyl)-vi-nyl]-oxazol-4-ylmethoxy}-phenyl)-oxazole-4-ylmethyl]-1H-[1,2,3]triazole A mixture of 97 mg (0.40 mmol) 4-(4-[1,2,3]triazol-1-ylmethyl-oxazol-2-yl)-phenol and 78 mg (0.24 mmol) cesium carbonate in 10 ml butanone was stirred at 60° C. for 30 min, then 140 mg (0.40 mmol) 4-chloromethyl-2-[2-(4-pentafluorosulfanyl-phenyl)-vinyl]-oxazole and 66 mg (0.40 mmol) potassium iodide were added and stirring at 60° C. continued over night. After evaporation, 15 ml water was added and the mixture extracted with three portions of 15 ml ethyl acetate. The combined organic layers were washed with 1N sodium hydroxide and water, dried over sodium sulfate and evaporated to yield 89 mg (40%) pure title compound as light yellow solid melting at 172-174° C.

MS: M=552.0(ESI+) $^1$H-NMR(400 MHz, D$_6$-DMSO): δ=5.13(s, 2H, NCH$_2$), 5.60(s, 2H, OCH$_2$), 7.19d, 2H, Ar—H), 7.36(d, 1H, vinyl), 7.62(d, 1H, vinyl), 7.76(s, 1H, triazole), 7.93(m, 6H, Ar—H), 8.18(s, 1H, triazole), 8.21(s, 1H, oxazole), 8.30(s, 1H, oxazole). $^{19}$F-NMR(376 MHz, D$_6$-DMSO): δ=63.6(d, 4F), 86.8(quintet, 1F).

LIST OF REFERENCES

Baselga, J., and Hammond, L. A., Oncology 63 (Suppl. 1) (2002) 6-16
Chan, A. C., and Shaw, A. S., Curr. Opin. Immunol. 8 (1996) 394-401
Larsen et al., Ann. Reports in Med. Chem., 1989, Chpt. 13
Ranson, M., and Sliwkowski, M. X., Oncology 63 (Suppl. 1) (2002) 17-24
Wilks et al., Prog. Growth Factor Res. 2 (1990) 97-111
Wright, C., et al., Br. J. Cancer 65 (1992) 118-121
Yarden, Y., and Ullrich, A., Annu. Rev. Biochem. 57 (1988) 443-478

What is claimed:

1. A compound of formula (I),

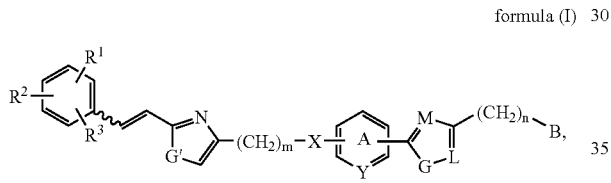

formula (I)

wherein
- R$^1$ and R$^2$ are each independently selected from the group consisting of hydrogen, halogen, nitro, cyano, —SF$_5$, —NR$^5$R$^{5'}$, R$^6$C(O)—, R$^7$O—, R$^7$S(O)$_x$—, R$^7$OC(O)—, R$^6$C(O)O—, R$^6$C(O)NR$^5$—, and R$^5$R$^{5'}$NC(O)—; and aliphatic hydrocarbon and
- R$^3$ is hydrogen or halogen;
- X is —O—;
- x is 0, 1 or 2;
- R$^5$ and R$^{5'}$ are independently of each other hydrogen or a group selected from the group consisting of aliphatic hydrocarbon, or R$^6$C(O)—;
- R$^6$ is hydrogen or a group selected from the group consisting of aliphatic hydrocarbon and R$^7$S—;
- R$^7$ is hydrogen or a group selected from the group consisting of aliphatic hydrocarbon, halogen, or R$^6$C(O)—;
- R$^5$, R$^{5'}$, R$^6$, R$^7$ are optionally further substituted;
- Y is =CH—;
- L is =CH—;
- M is =N—;
- G and G' —S— or —O—,
- m is an integer of 1 to 5;
- n is an integer of 1 to 10;
- B is imidazolyl or triazole; and
- ring A may optionally further be substituted;
- the symbol ⁓ means either (E)— or (Z)—configuration of the arylvinyl group whenever it is used; or their pharmaceutically acceptable salts.

2. The compound of claim 1 having the formula

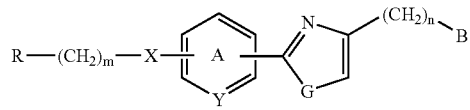

wherein
G is —O— or —S—;
X, Y and the cyclic group B are as in claim 1; m and n are each 1; and
R is a group of formula

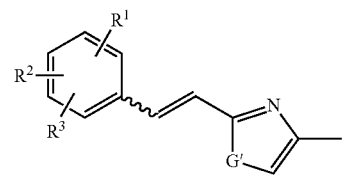

wherein
R$^1$, R$^2$, R$^3$, G' are as in claim 1.

3. The compound of claim 1 having the formula

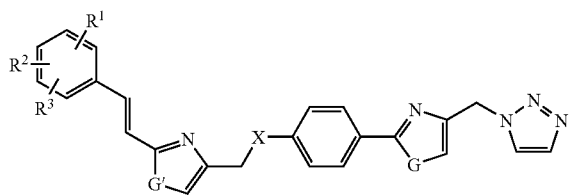

wherein
R$^1$ is selected from the group consisting of halogen; —O-alkyl; —S-alkyl; —S(O)-alkyl; —S(O)$_2$-alkyl; —N-alkyl; —SF$_5$ or alkyl, all alkyl groups being optionally once or several times substituted by halogen; and
R$^2$ is hydrogen or halogen; and
R$^3$ is hydrogen;
X, G and G' have the significance given in claim 1; or their pharmaceutically acceptable salts.

4. The compound of claim 3, wherein
R$^1$ is selected from the group consisting of halogen; —O-alkyl; —S-alkyl; —S(O)-alkyl; —S(O)$_2$-alkyl;— N-alkyl;—SF$_5$ or alkyl, all alkyl groups being optionally once or several times substituted by halogen;
R$^2$ is hydrogen or halogen;
R$^3$ is hydrogen; and
X and G are —O—; and
G' is —S—; or their pharmaceutically acceptable salts.

5. The compound of claim 4 having the formula
1-[2-(4-{2-[(E)-2-(4-Trifluoromethyl-phenyl)-vinyl]-thiazol-4-ylmethoxy}-phenyl) -oxazol-4-ylmethyl]-1H-[1,2,3]triazole.

6. The compound of claim 3, wherein
R$^1$ is selected from the group consisting of halogen; —O-alkyl; —S-alkyl; —S(O)-alkyl; —S(O)$_2$-alkyl; —N-alkyl; —SF$_5$ or alkyl, all alkyl groups being optionally once or several times substituted by halogen; and $R^2$ is hydrogen or halogen;
$R^3$ is hydrogen;
X, G' and G are all —O—; or their pharmaceutically acceptable salts.

7. The compound of claim 6 selected from the group consisting of 1-[2-(4-{2-(E)-2-(4-Trifluoromethyl-phenyl)-vinyl[-oxazol—4-ylmethoxy}-phenyl) -oxazol-4-ylmethyl]-1H-[1,2,3]triazole, 1-[2-(4-{2-[(E)-2-(4-Trifluoromethoxy-phenyl)-vinyl]-oxazol-4-ylmethoxy}phenyl) -oxazol-4-ylmethyl]-1H-[1,2,3]triazole, 1-[2-(4-{2-(E)-2-(4-Trifluoromethylsulfanyl-phenyl)-vinyl]-oxazol-4-ylmethoxy}-phenyl)-oxazol-4-ylmethyl]-1H-[1,2,3]triazole, 1-[2-(4-{2-[(E)-2-(4-Methoxy-phenyl)-vinyl]-oxazol-4ylmethoxy}-phenyl)-oxazol-4-ylmethyl]-1H-[1,2,3]triazole, 1-[2-(4-{2-(E)-2-(4-Chloro-phenyl)-vinyl]-oxazol-4-ylmethoxy}-phenyl)-oxazol-4-ylmethyl[-1H-[1,2,3]triazole, 1-[2-(4-{2-[(E)-2-(-4-Trifluoromethylsulfinyl-phenyl)-vinyl]-oxazol-4ylmethoxy}-phenyl)-oxazol-4-ylmethyl]-1H-[1,2,3]triazole, or 1-[2-(4-{2-(E)-2-(4-Pentafluorosulfanyl-phenyl)-vinyl]-oxazol-4ylmethoxy}-phenyl) -oxazol-4-ylmethyl]-1H-[1,2,3]triazole.

8. The compound of claim 3, wherein
$R^1$ is selected from the group consisting of halogen; —O-alkyl;—S-alkyl; —S(O)-alkyl; —S(O)$_2$-alkyl; —N-alkyl; —SF$_5$ or alkyl, all alkyl groups being optionally once or several times substituted by halogen; and
$R^2$ is hydrogen or halogen;
$R^3$ is hydrogen;
G is —S—;
G' is —S— or —O—; and
X is —O—or their pharmaceutically acceptable salts.

9. The compound of claim 8 having the formula: 1-[2-(4-{2-[(E)-2-(4-Trifluoromethyl-phenyl)-vinyl]-oxazol-4-ylmethoxy}-phenyl)-thiazol -4-ylmethyl]-1H-[1,2,3]triazole, or 1-[2-(4-{2-[(E)-2-(4-Trifluoromethyl-phenyl)-vinyl]-thiazol-4-ylmethoxy}-phenyl) -thiazol-4-ylmethyl]-1H-[1, 2,3]triazole.

10. The compound of claim 1 having the formula

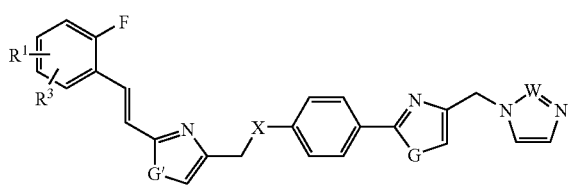

wherein
$R^1$ is selected from the group consisting of halogen; —O-alkyl; —S-alkyl; —S(O)-alkyl; —S(O)$_2$-alkyl; —N-alkyl; —SF$_5$ or alkyl, all alkyl groups being optionally once or several times substituted by halogen; and
$R^3$ is hydrogen;
W is —N=; or —C($R^8$)=; wherein
$R^8$ is hydrogen or $C_{1-6}$ alkyl, which is once or several times substituted by hydroxy;
X is —O—and
G' and G are independently—O—or —S—; or their pharmaceutically acceptable salts.

11. The compound of claim 10 selected from the group consisting of 2-[(E)-2-(2-Fluoro-4-trifluoromethyl-phenyl)-vinyl]-4-[4-(4-imidazol-1-ylmethyl -thiazol-2-yl)-phenoxymethyl]-oxazole, 2-[(E)-2-(2-Fluoro-4-trifluoromethyl-phenyl)-vinyl]-4-[4(4imidazol-1ylmethyl-oxazol-2-yl)-phenoxymethyl]-oxazole, 2-[(E)-2-(2-Fluoro-4-chloro-phenyl)-vinyl]-4-[4(4-imidazol-1-ylmethyl-oxazol-2yl)-phenoxymethyl]-oxazole, 1-[2-(4-{2-[(E)-2-(2-Fluoro-4-trifluoromethyl-phenyl)-vinyl]-oxazol-4-ylmethoxy}-phenyl)-oxazol-4-ylmethyl]-1H-[1,2,3]triazole 1-[2-(4-{2-[(E)-2-(4-Chloro-2-fluoro-phenyl)-vinyl]-oxazol-4-ylmethoxy}-phenyl) -oxazol-4-ylmethyl]-1H-[1,2,3]triazole, 1-[2-(4-{2-[(E)-2-(2-Fluoro-4-trifluoromethyl-phenyl)-vinyl]-oxazol-4-ylmethoxy}-phenyl)-thiazol-4-yhmethyl]-1H-[1,2,3]triazole, or 2-{1-[2-(4-{2-[(E)-2-(4-Choro-2-fluoro-phenyl)-vinyl]-oxazol-4ylmethoxy}-oxazol-4-ylmethyl]-1H-imidazol-2-yl}-ethanol.

12. The compound of claim 1

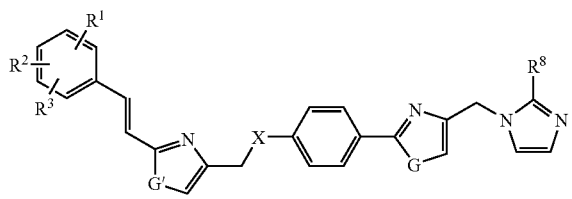

wherein
$R^1$ is selected from the group consisting of halogen; —O-alkyl; —S-alkyl; —S(O)-alkyl; —S(O)$_2$-alkyl; —N-alkyl; —SF$_5$ or alkyl, all alkyl groups being optionally once or several times substituted by halogen;
$R^2$ is hydrogen or halogen; and $R^3$ is hydrogen;
$R^8$ is hydrogen or $C_{1-6}$ alkyl, which is once or several times substituted by hydroxy;
X, G' and G have the significance given in claim 1; or their pharmaceutically acceptable salts.

13. The compound of claim 12, wherein
$R^1$ is selected from the group consisting of halogen; —O-alkyl; —S-alkyl; —S(O)-alkyl; —S(O)$_2$-alkyl-N-alkyl; —SF$_5$ or alkyl, all alkyl groups being optionally once or several times substituted by halogen; and
$R^2$ is hydrogen or halogen;
$R^3$ is hydrogen;
G' and G are independently —O— or—S—; and
X is —O—; or their pharmaceutically acceptable salts.

14. The compound of claim 13 having the formula: 1-[2-(4-{2-[(E)-2-(-4-Trifluoromethylsulfanyl-phenyl)-vinyl]-oxazol-4-ylmethoxy}-phenyl)-oxazol-4-ylmethyl]-1H-imidazole, or 1-[2-(4-{2-[(E)-2-(-4-Trifluoromethylsulfanyl-phenyl)-vinyl]-oxazol-4-ylmethoxy}-phenyl)-oxazol-4-ylmethyl]-1H-imidazole.

15. The compound of claim 1 having the formula

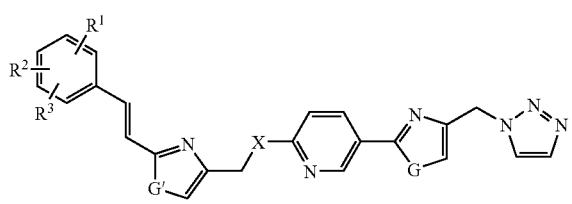

wherein
$R^1$ is selected from the group consisting of halogen; —)-alkyl; —S-alkyl; —S(O)-alkyl; —S(O)$_2$-alkyl; —N-alkyl; —SF$_5$ or alkyl, all alkyl groups being optionally once or several times substituted by halogen;

$R^2$ is hydrogen or halogen; and $R^3$ is hydrogen; and

X, G' and G have the significance given in claim 1; or their pharmaceutically acceptable salts.

16. A process for the manufacture of the compounds of formula (I), which comprises reacting compound of formula (II)

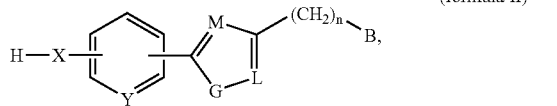

(formula II)

wherein B, X, Y, G, L, M and n have the meanings given in claim 1, with a compound of formula (III)

$$R\text{-}(CH_2)_m\text{-}E \qquad \text{(formula III)},$$

wherein

R has the meaning given in claim 2, m has the meaning given in claim 1, and E represents a suitable leaving group;

and thereafter isolating said formula (I) compound from its reaction mixture and if desired, converting said formula (I) compound into a pharmaceutically acceptable salt.

17. A pharmaceutical composition comprising a compound of formula (I) together with a pharmaceutically acceptable excipient.

18. A method of treating lung cancer which comprises administering to a patient in need thereof a therapeutically effective amount of a compound of claim 1.

* * * * *